United States Patent
Funaki et al.

(10) Patent No.: US 11,083,190 B2
(45) Date of Patent: *Aug. 10, 2021

(54) SOFT GEL SYSTEMS IN MODULATING STEM CELL DEVELOPMENT

(76) Inventors: Makoto Funaki, Media, PA (US); Paul A. Janmey, Media, PA (US); Jessamine Winer, Newbury Park, CA (US)

(*) Notice: Subject to any disclaimer, the term of this patent is extended or adjusted under 35 U.S.C. 154(b) by 721 days.

This patent is subject to a terminal disclaimer.

(21) Appl. No.: 12/452,268

(22) PCT Filed: Jun. 30, 2008

(86) PCT No.: PCT/US2008/008119
§ 371 (c)(1),
(2), (4) Date: Apr. 16, 2010

(87) PCT Pub. No.: WO2009/005769
PCT Pub. Date: Jan. 8, 2009

(65) Prior Publication Data
US 2010/0227399 A1    Sep. 9, 2010

Related U.S. Application Data

(60) Provisional application No. 60/929,488, filed on Jun. 29, 2007.

(51) Int. Cl.
*A01N 1/02*    (2006.01)
*C12N 5/077*    (2010.01)
(Continued)

(52) U.S. Cl.
CPC ............. *A01N 1/02* (2013.01); *A01N 1/0231* (2013.01); *C12N 5/0622* (2013.01);
(Continued)

(58) Field of Classification Search
CPC .. C12N 5/0622; C12N 5/0647; C12N 5/0653; C12N 5/0654; C12N 5/0663; A01N 1/02; A01N 1/0231
See application file for complete search history.

(56) References Cited

U.S. PATENT DOCUMENTS 6,927,060 B2 * 8/2005 Bickenbach et al. ......... 435/325
2002/0146821 A1 * 10/2002 Sanchez-Ramos et al. .. 435/368
(Continued)

FOREIGN PATENT DOCUMENTS

JP    2003-521900 A    7/2003
JP    2006-117633 A    5/2006
(Continued)

OTHER PUBLICATIONS

Engler et al, Matrix Elasticity Directs Stem Cell Lineage Specification, 2006, Cell 126:677-689.*
(Continued)

*Primary Examiner* — Sharmila G Landau
*Assistant Examiner* — Stephanie A McNeil
(74) *Attorney, Agent, or Firm* — Morgan, Lewis & Bockius LLP

(57) ABSTRACT

This invention provides gels and matrices having a rigidity in the range of 150-750 Pa, methods of manufacturing same, and method of preserving a mesenchymal stem cell population or studying mesenchymal stem cells, comprising same.

38 Claims, 14 Drawing Sheets

(51) Int. Cl.
- C12N 5/079 (2010.01)
- C12N 5/0789 (2010.01)
- C12N 5/09 (2010.01)
- C12N 5/0775 (2010.01)

(52) U.S. Cl.
CPC ......... *C12N 5/0647* (2013.01); *C12N 5/0653* (2013.01); *C12N 5/0654* (2013.01); *C12N 5/0663* (2013.01); *C12N 5/0693* (2013.01); *C12N 2500/38* (2013.01); *C12N 2500/42* (2013.01); *C12N 2501/39* (2013.01); *C12N 2533/30* (2013.01); *C12N 2533/52* (2013.01); *C12N 2533/56* (2013.01)

(56) References Cited

U.S. PATENT DOCUMENTS

| | | | |
|---|---|---|---|
| 2004/0082513 | A1 | 4/2004 | Hubbell et al. |
| 2004/0136977 | A1* | 7/2004 | Miyamoto ............... 424/94.63 |
| 2005/0058687 | A1 | 3/2005 | Guarino et al. |
| 2005/0164389 | A1 | 7/2005 | Sawyer et al. |
| 2005/0186261 | A1* | 8/2005 | Avelar et al. ............... 424/445 |
| 2006/0233748 | A1 | 10/2006 | Merzouk et al. |
| 2007/0026518 | A1 | 2/2007 | Healy et al. |
| 2007/0065415 | A1 | 3/2007 | Kleinsek et al. |
| 2007/0190646 | A1 | 8/2007 | Engler et al. |

FOREIGN PATENT DOCUMENTS

| | | |
|---|---|---|
| JP | 2007-504823 A | 3/2007 |
| JP | 2007-116926 A | 5/2007 |
| WO | 2001/49851 A1 | 7/2001 |
| WO | WO-2009005769 A2 | 1/2009 |
| WO | WO-2009005770 A1 | 1/2009 |

OTHER PUBLICATIONS

Pelham et al, Cell locomotion and focal adhesions are regulated by substrate flexibility, 1997, Proc. Natl. Acad. Sci., 94: 13661-13665.*

Conget et al, Phenotypical and Functional Properties of Human Bone Marrow Mesenchymal Progenitor Cells, 1999, Journal of Cellular Physiology 181:67-73.*

Markusen et al., Behavior of Adult Human Mesenchymal Stem Cells Entrapped in Alginate-GRGDY Beads, 2006, Tissue Engineering, 12(4): 821-83.*

Tse et al, Stiffness Gradients Mimicking In Vivo Tissue Variation Regulate Mesenchymal Stem Cell Fate, 2011, PLoS ONE 6(1): e15978.*

Saha et al, Substrate Modulus Directs Neural Stem Cell Behavior, 2008, Biophys J., 95(9):4426-38.*

Lee et al, Rewiring mesenchymal stem cell lineage specification by switching the biophysical microenvironment, 2014, Scientific Reports, 4(5188): 1-8.*

Versaevel et al, Super-resolution microscopy reveals LINC complex recruitment at nuclear indentation sites, 2014, Scientific Reports, 4: 7362 (Year: 2014).*

Chen, Po-Yang et al., "Hyaluronan preserves the proliferation and differentiation potentials of long-term cultured murine adipose-derived stromal cells," Biochemical and Biophysical Research Communication, vol. 360, pp. 1-6, Jun. 8, 2007.

Deng, Zhansheng, et al., "Culturing rabbit bone marrow stromal cells in vitro on the surface of fibrin glue," China Journal of Modern Medicine, vol. 13, No. 9, pp. 14-16, May 2003 (English abstract and translation included).

Ehninger, Armin, et al., "The bone marrow stem cell niche grows up: mesenchymal stem cells and macrophages move in," J. Exp. Med. vol. 208. No. 3, pp. 421-428, Mar. 14, 2011.

Li, Ling, et al., "Stem cell quiescence," Clin. Cancer Research; 17 (15), Aug. 1, 2011, (published online May 18, 2011).

Wang, Chelsia Q., et al., Runx family genes, niche, and stem cell quiescence, Blood cells, molecules, and diseases, vol. 44, pp. 275-286 (2010).

Winer, Jessamine P., et al., "Bone marrow-derived human mesenchymal stem cells become quiescent on soft substrates but remain responsive to chemical or mechanical stimuli," Tissue Engineering, vol. 15, No. 1, (2009), published online Jul. 30, 2008.

Yeung, Tony, et al., "Effects of substrate stiffness on cell morphology, cytoskeletal structure, and adhesion," Cell Motility and the Cytoskeleton, vol. 60, pp. 24-34 (2005).

Zhou, Zhu-Juan, et al., "Effect of low serum culture on the synchrony of cell cycle of mesenchymal stem cells," Chinese Journal of Cellular and Molecular Immunology, vol. 23, No. 4, pp. 369-371, Apr. 2007. (English Abstract included).

Baxter, et al., "Study of telomere length reveals rapid aging of human marrow stromal cells following in vitro expansion," Stem Cells, 22(5): 675-682 (Sep. 2004).

Bearzi, et al., "Human cardiac stem cells," Proc. Natl. Acad. Sci. (USA), 104(35): 14068-14073 (Aug. 2007).

Beltrami, et al. "Adult cardiac stem cells are multipotent and support myocardial regeneration," Cell, 114: 763-776 (Sep. 2003).

Beningo, et al., "Responses of fibroblasts to anchorage of dorsal extracellular matrix receptors," Proc. Natl. Acad. Sci. (USA), 101(52): 18024-18029 (Dec. 2004).

Blau, et al., "The evolving concept of a stem cell: entity or function?", Cell, 105: 829-841 (Jun. 2001).

Bonab, et al., "Aging of mesenchymal stem cell in vitro," BMC Cell Biology, 7(14): 1-7 (Mar. 2006).

Bosnakovski, et al, "Chondrogenic differentiation of bovine bone marrow mesenchymal stem cells (MSCs) in different hydrogels: influence of collagen type II extracellular matrix on MSC chondrogenesis," Biotechnology and Bioengineering, 93(6): 1152-1163 (pub. online Feb. 2006).

Butler, et al., "Extracellular matrix proteins of dentine," Ciba Foundation Symposium 205: 107-115; Discussion at 115-117 (1997).

Carnegie and Cabaca, "Extracellular matrix composition and resilience: two parameters that influence the in vitro migration and morphology of rat inner cell mass-derived cells," Biology of Reproduction, 48(2): 287-299 (Feb. 1993).

Engler, et al., "Matrix elasticity directs stem cell lineage specification," Cell, 126(4): 677-689 (Aug. 2006).

Engler, et al., "Microtissue elasticity: measurements by atomic force microscopy and its influence on cell differentiation," Methods in Cell Biology, 83: 521-545 (Jul. 2007).

Engler, et al., "Myotubes differentiate optimally on substrates with tissue-like stiffness: pathological implications for soft or stiff microenvironments," J. Cell. Biol., 166(6): 877-887 (Sep. 2004).

Friedenstein, et al., "Fibroblast precursors in normal and irradiated mouse hematopoietic organs," Exp. Hematology, 4: 267-274 (1976).

Friedenstein, et al., "The development of fibroblast colonies in monolayer cultures of guinea-pig bone marrow and spleen cells," Cell Tissue Kinet. 3: 393-403 (1970).

Funaki, et al., "Separation of insulin signaling into distinct GLUT4 translocation and activation steps," Mol. Cell Biol., 24(17): 7567-7577 (Sep. 2004).

Georges, et al., "Matrices with compliance comparable to that of brain tissue select neuronal over glial growth in mixed cortical cultures," Biophysical Journal, 90(8): 3012-3018 (Apr. 2006).

Gordon, et al., "Recovery of human mesenchymal stem cells following dehydration and rehydration," Cryobiology, 43(2): 182-187 (Sep. 2001).

Guo, et al., "Substrate rigidity regulates the formation and maintenance of tissues," Biophysical Journal, 90(6): 2213-2220 (Mar. 2006).

Hermann, et al., "Efficient generation of neural stem cell-like cells from adult human bone marrow stromal cells," J. of Cell Science, 117(19): 4411-4422 (Sep. 2004).

Hirai, et al., "Geranylgeranylated Rho small GTPase(s) are essential for the degradation of $p27^{Kip1}$ and facilitate the progression from $G_1$ to S phase in growth-stimulated rat Frtl-5 cells," J. Biol. Chem., 272(1): 13-16 (Jan. 1997).

(56) References Cited

OTHER PUBLICATIONS

Jori, et al., "Molecular pathways involved in neural in vitro differentiation of marrow stromal stem cells," J. Cell. Biochem., 94: 645-655 (2005).
Kassem, "Stem cells—potential therapy for age-related diseases," Ann. N.Y. Acad. Sci., 1067: 436-442 (pub. online May 2006).
Kondo, et al., "Sonic hedgehog and retinoic acid synergistically promote sensory fate specification from bone marrow-derived pluripotent stem cells," Proc. Natl. Acad. Sci. (USA), 102(13): 4789-4794 (Mar. 2005).
Kundu and Putnam, "Vitronectin and collagen I differentially regulate osteogenesis in mesenchymal stem cells," Biochem. Biophys. Res. Commun., 347: 347-357 (2006).
Laufs, et al., "3-Hydroxy-3-methylglutaryl-CoA reductase inhibitors attenuate vascular smooth muscle proliferation by preventing Rho GTPase-induced down-regulation of $p27^{Kip1}$," J. Biol. Chem., 274(31): 21926-21931 (Jul. 1999).
Leri, et al., "Cardiac stem cells and mechanisms of myocardial regeneration," Physiological Reviews, 85(4): 1373-1416 (Oct. 2005).
Linke, et al., "Stem cells in the dog heart are self-renewing, clonogenic, and multipotent and regenerate infarcted myocardium, improving cardiac function," Proc. Natl. Acad. Sci. (USA), 102(25): 8966-8971 (Jun. 2005).
Liu, et al., "Telomerase deficiency impairs differentiation of mesenchymal stem cells," Exp. Cell Res., 294(1): 1-8 (Mar. 2004).
Lo, et al., "Cell movement is guided by the rigidity of the substrate," Biophysical Journal, 79(1): 144-152 (Jul. 2000).
Lu, et al., "CDC42 and Rac1 are implicated in the activation of the Nef-associated kinase and replication of HIV-1," Current Biology, 6(12): 1677-1684 (Dec. 1996).
McBeath, et al., "Cell shape, cytoskeletal tension, and RhoA regulate stem cell lineage commitment," Developmental Cell, 6: 483-495 (Apr. 2004).
Messina, et al., "Isolation and expansion of adult cardiac stem cells from human and murine heart," Circulation Research, 95(9): 911-921 (Oct. 2004).
Minguell, et al., "Mesenchymal stem cells," Exp. Biology and Medicine, 226(6): 507-520 (Jun. 2001).
Nardi and Meirelles, "Mesenchymal stem cells: isolation, in vitro expansion and characterization," Handbook of Exp. Pharmacology, 174: 249-282 (2006).
Neth, et al., "Wnt signaling regulates the invasion capacity of human mesenchymal stem cells," Stem Cells, 24(8): 1892-1903 (Aug. 2006).
O'Shea, et al., "Role of the extracellular matrix protein thrombospondin in the early development of the mouse embryo," Cell Biology, 111(6), Part 1: 2713-2723 (Dec. 1990).
Oh, et al., "Cardiac progenitor cells from adult myocardium: homing, differentiation, and fusion after infarction," Proc. Natl. Acad. Sci. (USA), 100(21): 12313-12318 (Oct. 2003).
Okabe, et al., "'Green mice' as a source of ubiquitous green cells," FEBS Letters, 407: 313-319 (1997).
Olson, et al., "Signals from Ras and Rho GTPases interact to regulate expression of $p21^{Waf1/Cip1}$," Nature, 394(6690): 295-299 (Jul. 1998).
Otaki, et al., "Mesenchymal progenitor cells in adult human dental pulp and their ability to form bone when transplanted into immunocompromised mice," Cell Biology International, 31(10): 1191-1197 (Oct. 2007).
Pelham, Jr. and Wang, "Cell locomotion and focal adhesions are regulated by substrate flexibility," Proc. Natl. Acad. Sci. (USA), 94(25): 13661-13665 (Dec. 1997). Corrections: Proc. Natl. Acad. Sci. (USA), 95: 12070-12071 (1998).
Pittenger, et al., "Multilineage Potential of Adult Human Mesenchymal Stem Cells," 284(5411): 143-147 (Apr. 1999).
Qui, et al., "A roll for Rho in Ras transformation," Proc. Natl. Acad. Sci. USA, 92(25): 11781-11785 Cell Biology (Dec. 1995).
Reiser, et al., "Potential of mesenchymal stem cells in gene therapy approaches for inherited and acquired diseases," Expert Opinion on Biological Therapy, 5(12): 1571-1584 (Dec. 2005).
Sahai, et al., "Cross-walk between Ras and Rho signaling pathways in transformation favours proliferation and increased motility," The EMBO Journal, 20(4): 755-766 (Feb. 2001).
Sakaguchi, et al., "Comparison of human stem cell derived from various mesenchymal tissues," Arthritis & Rheumatism, 52(8): 2521-2529 (Aug. 2005).
Sakaguchi, et al., "Suspended cells from trabecular bone by collagenase digestion become virtually identical to mesenchymal stem cells obtained from marrow aspirates," Blood, 104(9): 2728-2735 (Nov. 2004).
Salasznyk, et al., "Adhesion to vitronectin and collagen I promotes osteogenic differentiation of human mesenchymal stem cells," J. Biomedicine and Biotechnology, 2004(1): 24-34 (2004).
Schenke-Layland, et al., "Collagen IV induces trophoectoderm differentiation of mouse embryonic stem cells," Stem Cells, 25(6): 1529-1538 (pub. online Mar. 2007).
Sekiya, et al., "Adipogenic differentiation of human adult stem cells from bone marrow stroma (MSCs)," J. Bone and Mineral Research, 19(2): 256-264 (Feb. 2004).
Sekiya, et al., "BMP-6 enhances chondrogenesis in a subpopulation of human marrow stromal cells," Biochemical and Biophysical Research Communications, 284(2): 411-418 (Jun. 2001).
Shao and Lazar, "Peroxisome proliferator activated receptor gamma, CCAAT/enhancer-binding protein alpha, and cell cycle status regular the commitment to adipocyte differentiation," J. Biol. Chem., 272(34): 21473-21478 (Aug. 1997).
Sottile, et al., "Stem cell characteristics of human trabecular bone-derived cells," Bone, 30(5): 699-704 (May 2002).
Tarnowski and Sieron, "Adult stem cells and their ability to differentiate," Medical Science Monitor, 12(8): RA154-163 (Aug. 2006).
Urbanek, et al., "Myocardial regeneration by activation of multipoint cardiac stem cells in ischemic heart failure," Proc. Natl. Acad. Sci. (USA), 102(24): 8692-8697 (Jun. 2005).
Urbanek, et al., "Stem cell niches in the adult mouse heart," Proc. Natl. Acad. Sci. (USA), 103(24): 9226-9231 (Jun. 2006).
Urs, et al., "Gene expression profiling in human preadipocytes and adipocytes by microarray analysis," J. Nutrition, 134(4): 762-770 (Apr. 2004).
Williams, et al, "Conformational states of fibronectin. Effects of pH, ionic strength, and collagen binding," J. Biol. Chem., 257(24): 14973-14978 (Dec. 1982).
Woodbury, et al., "Adult rat and human bone marrow stromal cells differentiate into neurons," J. Neuroscience Research, 61(4): 364-370 (Aug. 2000).
Yeung, et al., "Effects of substrate stiffness on cell morphology, cytoskeletal structure, and adhesion," Cell Motility Cytoskeleton, 60(1): 24-34 (Jan. 2005).
Zigmond, "A method for movement," Nature Cell Biology, 1: E12 (May 1999).
Paz, et al., *A New Mechanism of Action for the Anticancer Drug Mitomycin C: Mechanism-Based Inhibition of Thioredoxin Reductase*, Chem. Res, Toxicol 25:1502-15 (2012).
Bartek, et al., "Checking on DNA damage in S phase," Nature Publishing Group, vol. 5, pp. 792-804, Oct. 2004.
Cobrinik, "Pocket proteins and cell cycle control," Oncogene 24, pp. 2796-2809, 2005.
Collinsworth, et al., "Apparent elastic modulus and hysteresis of skeletal muscle cells throughout differentiation," Am J Physiol Cell Physiol 283: C1219-C1227, Jun. 5, 2002.
Gautreau, et al., "Characterizing viscoelastic properties of polyacrylamide gels," A Major Qualifying Project Report, Apr. 27, 2006.
Kamgoué, et al., "Estimation of cell young's modulus of adherent cells probed by optical and magnetic tweezers: influence of cell thickness and bead immersion," Journal of Biomechanical Engineering, vol. 129, pp. 523-530, Aug. 2007.
Klein, et al., "Cell-cycle control by physiological matrix elasticity and in vivo tissue stiffening," Current Biology 19, pp. 1511-1518, Sep. 29, 2009.
Lara-Gonzalez, et al., "The spindle assembly checkpoint," Current Biology 22, R966-R980, Nov. 20, 2012.

(56) References Cited

OTHER PUBLICATIONS

Mikule, et al., "Loss of centrosome integrity induces p38-p53-p21-dependent G1-S arrest," Nature Cell Biology, vol. 9, No. 2, Feb. 2007 (published online Dec. 24, 2006; DOI: 10.1038/ncb1529).
Non-Final Office Action in U.S. Appl. No. 12/452,281, dated Sep. 26, 2013.
Novák, et al, "Checkpoint in the cell cycle," Encyclopedia of Life Sciences, pp. 1-8, 2002.
Orford, et al., "Deconstructing stem cell self-renewal: genetic insights into cell-cycle regulation," Nature Reviews/Genetics, vol. 9, Feb. 2008.
Park, et al., "Increased caveolin-1, a cause for the declined adipogenic potential of senescent human mesenchymal stem cells," Mechanisms of Ageing and Development, 126, pp. 551-559, 2005.
Shimura, et al., "Micronuclei formation and aneuploidy induced by Vpr, and accessory gene of human immunodeficiency virus type 1" FASEB J. 13, pp. 621-637, 1999.
Steinbrück, et al., "Effects of artesunate on cytokinesis and G2/M cell cycle progression of tumour cells and budding yeast," Cancer Genomics & Proteomics 7: pp. 337-346, 2010.
Topham, et al., "Mitosis and apoptosis: how is the balance set?" SciVerse ScienceDirect, Current Opinion in Cell Biology 2013, 25: pp. 780-785.
Xie, et al., "Cells deficient in oxidative DNA damage repair genes Myh and Ogg1 are sensitive to oxidants with increased G2/M arrest and multinucleation," Carcinogenesis, vol. 29, No. 4, pp. 722-728, 2008.
Zhang, et al., "Disruption of G1-phase phospholipid turnover by inhibition of Ca2+-independent phospholipase A2 induces a p53-dependent cell-cycle arrest in G1 phase," Journal of Cell Science 119, pp. 1005-1015, 2006.
Notice of Submission of Information filed Feb. 6, 2014, in JP Application No. 2010-514846.
Pronova™ $SLG_{100}$ Product Specification Bulletin, FMC Corporation (2002).
"A World of Possibilities Lies Just Below the Surface—Alginates," FMC BioPolymer brochure, FMC Corporation (2003).
Faustman & Davis, "Stem cells in the spleen: Therapeutic potential for Sjogren's syndrome, type 1 diabetes, and other disorders," 42(10) Int'l J. Biochem. Cell Biol. 1576-79 (2010).
Georges et al., "Increased stiffness of the rat liver precedes matrix deposition: implications for fibrosis," 293 Am. J. Physiol. Gastrointest. Liver Physiol. G1147-54 (2007).
Kordes & Haussinger, "Hepatic stem cell niches," 123(5) J. Clinical Invest. 1874-80 (2013).
Nicolle et al., "Shear mechanical properties of the spleen: Experiment and analytical modelling," 9 J. Mech. Behav. Biomed. Mat. 130-36 (2012).
Eyckmans et al., "Sticky mechanical memory," 13 Nature Materials 542-43 (2014).
Trappmann et al., "Extracellular-matrix tethering regulates stem-cell fate," 11 Nature Materials 642-49 (2012).
Wang et al., "Cell Adhesion and Mechanical Stimulation in the Regulation of Mesenchymal Stem Cell Differentiation," 17(7) J. Cell. Mol. Med. 823-32 (2013).
Carreau et al., "Why is the partial oxygen pressure of human tissues a crucial parameter? Small molecules and hypoxia," 15(6) J. Cell. Mol. Med. 1239-53 (2011).
Chow et al., "Modeling $pO_2$ Distributions in the Bone Marrow Hematopoietic Compartment. II. Modified Kroghian Models," 81 Biophys. J. 685-96 (2001).
Dombrowski et al., "FGFR1 Signaling Stimulates Proliferation of Human Mesenchymal Stem Cells by Inhibiting the Cyclin-Dependent Kinase Inhibitors p21wai1 and $p27^{Waf1\ and\ p27Kip1}$," 31 Stem Cells 2724-36 (2013).
Even-Ram et al., "Matrix Control of Stem Cell Fate," 126 Cell 645-47 (2006).

Jin et al., "Mesenchymal stem cells cultured under hypoxia escape from senescence via down-regulator of p16 and extracellular signal regulated kinase," 391 Biochem. Biophys. Res. Comm. 1471-76 (2010).
Wesierska-Gadek et al., "Role of P53 Tumor Suppressor in Ageing: Regulation of Transient Cell Cycle Arrest and Terminal Senescence," 56(1) J. Physiol. Pharmacol. 15-28 (2005).
Xu et al., "Enrichment of cancer stem cell-like cells by culture in alginate gel beads," 177 J. Biotech. 1-12 (2014).
Buxboim et al., "How deeply cells feel: methods for thin gels," Author manuscript, available in PubMed Central May 19, 2011, published as 22(19) J. Phys. Condens. Matter 194116 (2010).
English translation of Zhou et al., "Effect of low serum culture on the synchrony of cell cycle of mesenchymal stem cells," 23(4) Chin. J. Cell. Mol. Immunol. 369-71 (2007.
Extended European Search Report in EP Application No. 15196849. 2, dated May 2, 2016.
Horii, "Influence of Niche on Proliferation and Differentiation of Mesenchymal Stem Cells," Master's Thesis, Department of Chemistry for Materials, Faculty of Engineering, Mie University (2001).
Information Statement in Japanese Application No. 2014-222238, dated Feb. 29, 2016.
Information Statement in Japanese Application No. 2014-222242, dated Feb. 29, 2016.
Loosli et al., "Cytoskeleton reorganization of spreading cells on micro-patterned islands: a functional model," 368 Phil. Trans. R. Soc. A 2629-52 (2010).
Murphy-Ullrich, "The de-adhesive activity of matricellular proteins: is intermediate cell adhesion an adaptive state?" 107(7) J. Clin. Investigation 785-90 (2001).
Ogura et al., "Differentiation of the human mesenchymal stem cells derived from bone marrow and enhancement of cell attachment by fibronectin," 46(4) J. Oral Science 207-13 (2004).
Sallustio et al., "miR-1915 and miR-1225-5p Regulate the Expression of CD133, PAX2 and TLR2 in Adult Renal Progenitor Cells," 8(7) Plos One e68296 (2013).
Sarker et al., "Alginate-based hydrogels with improved adhesive properties for cell encapsulation," 78 Int'l J. Bio. Macromolecules 72-78 (2015).
Titushkin et al., "Altered osteogenic commitment of human mesenchymal stem cells by ERM protein-dependent modulation of cellular biomechanics," 44 J. Biomechanics 2692-98 (2011).
Van Den Dolder et al., "Effect of Fibronectin- and Collagen I-Coated Titanium Fiber Mesh on Proliferation and Differentiation of Osteogenic Cells," 9(3) Tissue Eng. 505-15 (2003).
Zhao et al., "Biomarkers of Cell Senescence Assessed by Imaging Cytometry," Author manuscript, available in PubMed Central Jan. 1, 2014, published in 965 Methods Mol. Biol. 83-92 (2013).
Non-Final Office Action in U.S. Appl. No. 12/452,281, dated Nov. 16, 2012.
Conget et al,. "Phenotypical and Functional Properties of Human Bone Marrow Mesenchymal Progenitor Cells," 181 J. Cell. Physiol. 67-73 (1999).
Li et al., "Extracellular matrix with the rigidity of adipose tissue helps 3T3-L1 adipocytes maintain insulin responsiveness," 56 J. Med. Investigation 142-49 (2009).
Wang et al., "Clinical applications of mesenchymal stem cells," 5 J. Hematol. & Oncol. 19-27 (2012).
Asahara et al., *Stem cell therapy and gene transfer for regeneration*, Gene Therapy, 7:451-457 (2000).
Blagosklonny, *Cell cycle arrest is not senescence*, Aging 3(2):94-101 (Feb. 2011).
Braun, et al., *Serum-Nutrient Starvation Induces Cell Death Mediated by Bax and Puma That Is Counteracted by p21 and Unmasked by Bcl-xL Inhibition*, PLoS One, 6(8):e23577;1-11 (Aug. 2011).
Cheung, et al., *Molecular regulation of stem cell quiescence*, Molecular Cell Biology, 14:329-340 (Jun. 2013).
Coller, et al., *A New Description of Cellular Quiescence*, PloS Biology, 4(3):e83;0329-0349 (Mar. 2006).
Junqueira, et al., *Basic Histology*, fig.5-29, p. 119 (7th ed., Appleton & Lange 1992).

(56) References Cited

OTHER PUBLICATIONS

Kandow, et al., *Polyacrylamide Hydrogels for Cell Mechanics: steps toward optimization and alternative uses*, Methods in Cell Biology, 83:29-46 (2007).
Kong, et al., *Regulation of Senescence in Cancer and Aging*, Journal of Aging Research 2011:963172;1-15 (2011).
Omoto, et al., The Use of Human Mesenchymal Stem Cell-Derived Feeder Cells for the Cultivation of Transplantable Epithelial Sheets, Investigative Ophthalmology & Visual Science, 50(5):2109-2115 (May 2009).
Paz, et al., *A New Mechanism of Action for the Anticancer Drug Mitomycin C: Mechanism-Based Inhibition of Thioredoxin Reductase*, Chem. Res, Toxicol., 25:1502-1511 (2012).
Sedivy, *Can ends justify the means?: Telomeres and the mechanisms of replicative senescence and immortalization in mammalian cells*, Proc. Natl. Acad. Sci., 95:9078-9081 (Aug. 1998).
Young, et al., *Retention of Quiescent Hematopoietic Cells With High Proliferative Potential During Ex Vivo Stem Cell Culture*, Blood, 87(2):545-556 (Jan. 1996).
Final Office Action in U.S. Appl. No. 12/452,281, dated Apr. 22, 2013.

\* cited by examiner

GLASS                    SOFT GELL

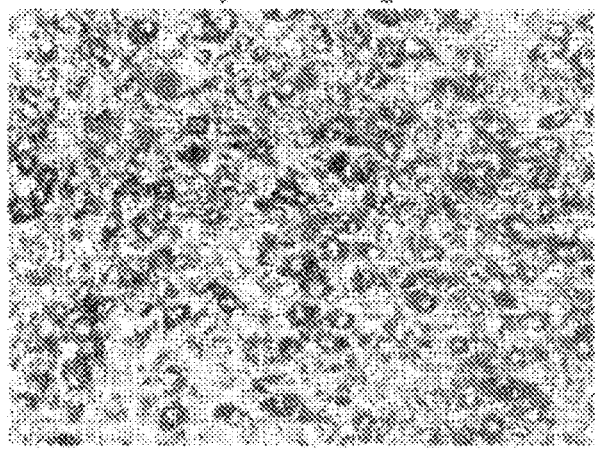
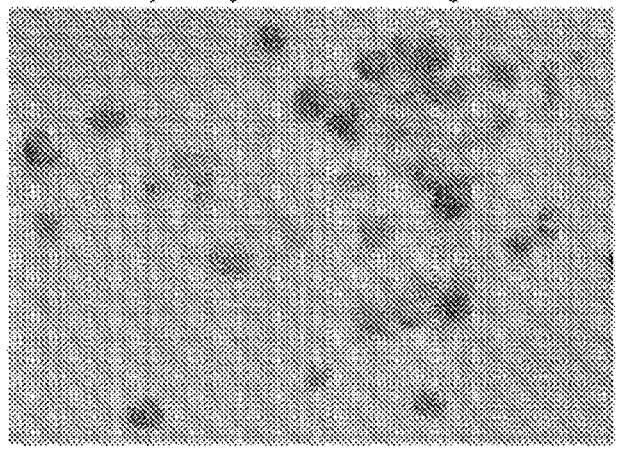
FIGURE 3B

FIGURE 13A-B

SOFT GEL SYSTEMS IN MODULATING STEM CELL DEVELOPMENT

FIELD OF INVENTION

This invention provides methods of modulating stem cell development using soft-gels. Specifically, the invention provides methods, compositions and devices for modulating the development of stem cells, using gels having optimized viscoelastic properties.

BACKGROUND OF THE INVENTION

Adult mesenchymal stem cells have the ability to self-renew and differentiate into multiple cell lineages of mesenchymal tissues. Therefore, clinical applications of these cells, such as replacement of damaged tissues or carriers for anti-cancer agents, have been considered. Applications of adult mesenchymal stem cells are still limited to preclinical stage at this time, in part because of rapid aging of these cells ex vivo, which limits their expansion and engineering. Immortalizing mesenchymal stem cells by telomerase transduction is reported to overcome issues associated with accelerated aging. However, their ability of unlimited self-renewal may lead to an out-of-control growth, once they are implanted into tissues. In fact, transformation of telomerase-transduced mesenchymal stem cells was observed in in vitro settings.

Thus, regulation of the growth of adult mesenchymal stem cells is one of the key steps toward their clinical applications.

SUMMARY OF THE INVENTION

This invention provides methods of modulating stem cell development using soft-gels. Specifically, the invention provides methods, compositions and devices for modulating the development of stem cells, using gels having optimized viscoelastic properties.

In one embodiment, the present invention provides a method of manufacturing a coated polyacrylamide gel having a rigidity in a range of 150-750 Pa, comprising the steps of polymerizing a composition comprising acrylamide and bisacrylamide, said composition having an acrylamide:bisacrylamide mixture ratio of between 100:1 and 30:1; and coating said soft polyacrylamide gel with a composition comprising a collagen type I and a fibronectin.

In another embodiment, the invention provide s a method of manufacturing a fibrin matrix having a rigidity in a range of 0.1-2.5 kPa, comprising the steps of polymerizing a composition comprising a fibrin or fibrinogen protein, thereby producing a soft fibrin matrix, wherein the concentration of said fibrin or fibrinogen protein in said soft fibrin matrix is 1-20 mg/ml, and coating said soft fibrin matrix with a composition comprising an adhesion protein.

In another embodiment, the present invention provides a method of preserving a mesenchymal stem cell population, said method comprising the step of culturing said mesenchymal stem cell population in a gel matrix having a rigidity in a range of 0.1-2.5 kPa.

In another embodiment, the present invention provides a method of inducing differentiation of a mesenchymal stem cell population into an adipocyte population, said method comprising the step of culturing said mesenchymal stem cell population in the presence of an apparatus containing (a) a gel or matrix having a rigidity in a range of 150-750 Pa and (b) an adipocyte induction medium, thereby inducing differentiation of a mesenchymal stem cell population into a cell type of interest.

In another embodiment, the present invention provides an apparatus for modulating growth of a mesenchymal stem cell comprising: a gel matrix having a rigidity in a range of 150-750 Pa; and an adipocyte induction medium, wherein said gel or matrix is coated with a type 1 collagen, a fibronectin, or a combination thereof.

In another embodiment, the present invention provides a gel matrix comprising a gelling agent and an acrylamide-bisacrylamide mixture wherein said gel matrix is coated with a type I collagen, a fibronectin, or a combination thereof and having a rigidity in a range of 150-750 Pa.

In one embodiment, the invention provides a method of modulating development of a mesenchymal stem cell, comprising the step of suspending the mesenchymal stem cell in a gel matrix comprising a gelling agent wherein said gel matrix is coated with a type 1 collagen, a fibronectin, or a combination thereof and wherein said gel matrix is maintained at a predetermined rigidity; and exposing the gel matrix to a growth modulating factor.

In another embodiment, the invention provides a method for inducing or maintaining quiescence and sustaining biological activity in a somatic stem cell ex vivo, comprising: contacting the somatic stem cell with a gel matrix comprising an extracellular material that bind to integrin on the membrane of the somatic stem cell, said gel matrix having a substantially similar elasticity to the elasticity of the predominant in vivo biological microenvironment of the somatic stem cell of the same type in vivo; and providing the somatic stem cell with nutrient material for sustaining biological activity of the somatic stem cell ex vivo.

BRIEF DESCRIPTION OF THE FIGURES

FIGS. 3A and 3B show the effect of matrix rigidity on adipocyte differentiation. FIG. 3A depicts a graph of percent positive cells (First bar in each series: Oil Red O-staining. Second bar: PPARγ2 staining). FIG. 3B depicts morphologies of cells seeded on glass and soft gel.

DETAILED DESCRIPTION OF THE INVENTION

Figure 1A:
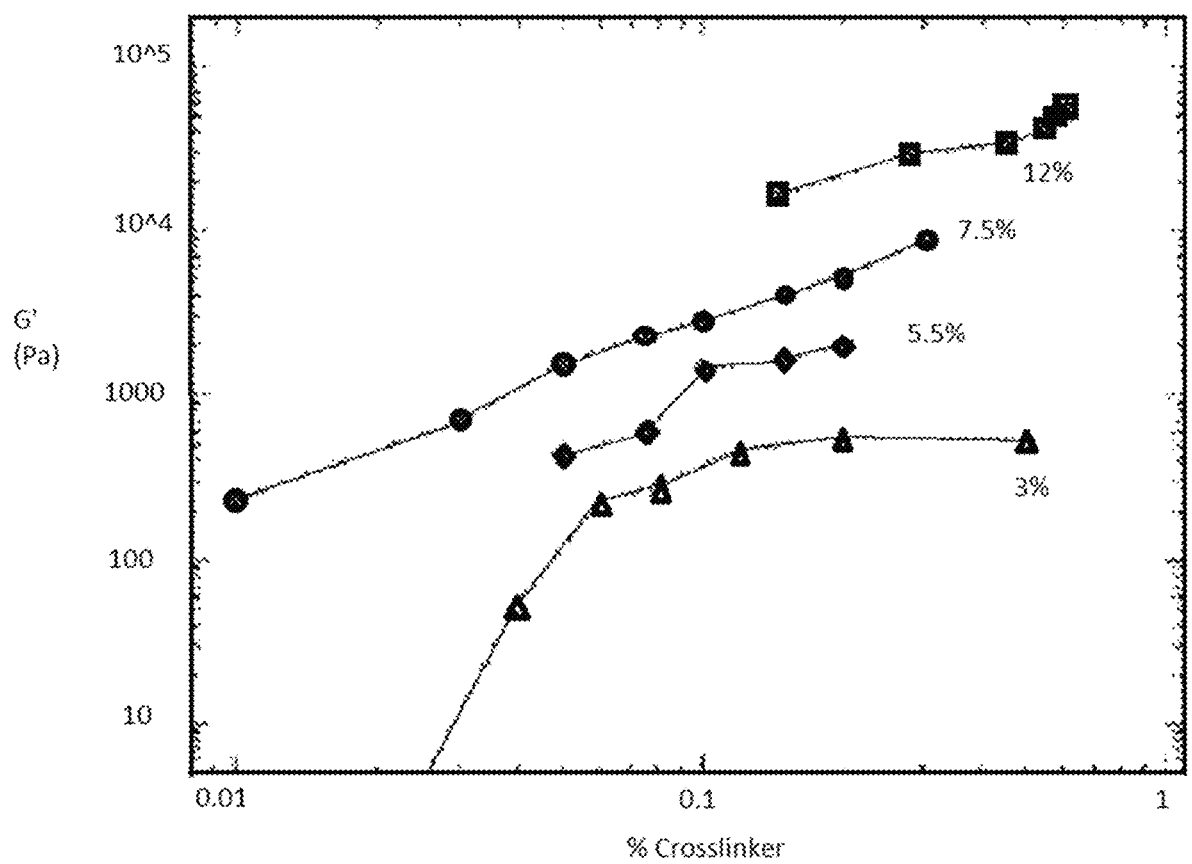
FIG. 1. A. Mechanical properties of polyacrylamide substrates. The shear modulus of polyacrylamide gels with a range of acrylamide (indicated as percents near data lines) to bisacrylamide (indicated as crosslinker) proportions was measured. The shear modulus (G'), expressed in Pascal, increases at constant polymer mass with increasing crosslinker. Increasing the concentration of acrylamide from 3 to 12% also creates a large stiffness range from 10 to 50,000 Pa. The solid line denotes the theoretical stiffness of a rubberlike network if every crosslink was elastically effective. B. Cell shape and F-actin structure of hMSC on stiff or soft matrices. C. Cell shape and F-actin structure of hMSC on soft gels and glass.

This invention provides gels and matrices having a rigidity in the range of 0.01-50 kPa, methods of manufacturing same, and method of preserving a mesenchymal stem cell population or studying mesenchymal stem cells, comprising same.

In one embodiment, provided herein is a method of manufacturing a polyacrylamide gel with a rigidity in a range of 150-750 Pa, comprising the steps of polymerizing a composition comprising acrylamide and bisacrylamide, thereby producing a soft polyacrylamide gel, and coating the soft polyacrylamide gel with a composition comprising a collagen type I and a fibronectin, thereby manufacturing a polyacrylamide gel having a rigidity in a range of 150-750 Pa. In another embodiment, the composition has an acrylamide: bisacrylamide mixture ratio of between 100:1 and 30:1. In another embodiment, the gel has an acrylamide: bisacrylamide mixture ratio of between 100:1 and 30:1. In another embodiment, the composition a total acrylamide concentration of 3-5%. In another embodiment, the gel or matrix has a total acrylamide concentration of 3-5%. In another embodiment, the composition is a solution. In another embodiment, the composition is a suspension. In another embodiment, the composition is any other type of composition known in the art. Each possibility represents a separate embodiment of the present invention.

In another embodiment, provided herein is a method of manufacturing a fibrin matrix with a rigidity in a range of 150-750 Pa, comprising the steps of polymerizing a composition comprising a fibrin or fibrinogen protein, thereby producing a soft fibrin matrix, wherein the concentration of the fibrin or fibrinogen protein in the soft fibrin matrix is 3-10 mg/mL, and coating the soft fibrin matrix with a composition comprising an adhesion protein, thereby manufacturing a fibrin matrix having a rigidity in a range of 150-750 Pa.

In another embodiment, provided herein is a method of preserving a mesenchymal stem cell population, the method comprising the step of culturing the mesenchymal stem cell population in a gel or matrix with a rigidity in a range of 150-750 Pa, thereby preserving a mesenchymal stem cell population. In another embodiment, the step of culturing is performed in the absence of chemical induction. In another embodiment, the step of culturing is performed in the absence of an induction medium. Each possibility represents a separate embodiment of the present invention.

In another embodiment, provided herein is a method of preserving a mesenchymal stem cell, the method comprising the step of culturing the mesenchymal stem cell population in a gel or matrix with a rigidity in a range of 150-750 Pa, thereby preserving a mesenchymal stem cell. In another embodiment, the step of culturing is performed in the absence of chemical induction. In another embodiment, the step of culturing is performed in the absence of an induction medium. Each possibility represents a separate embodiment of the present invention.

In another embodiment, provided herein is a method of inducing quiescence of a transformed cell, comprising the step of culturing the transformed cell in a gel or matrix of the present invention, thereby inducing quiescence of a transformed cell. In another embodiment, the transformed cell is a cancer cell. In another embodiment, the transformed cell is a neoplastic cell. In another embodiment, the transformed cell is any other type of transformed cell known in the art. Each possibility represents a separate embodiment of the present invention.

In another embodiment of methods and compositions of the present invention, the telomerase length of the mesenchymal stem cell population is maintained. "Maintained" refers, in another embodiment, to a lack of substantial change in the length. In another embodiment, the term refers to a lack of measurable change in the length. In another embodiment, the term refers to a lack of sufficient change in the length to affect proliferative capacity. Each possibility represents a separate embodiment of the present invention.

In another embodiment of methods and compositions of the present invention, the mesenchymal stem cell population is maintained in a quiescent state. "Quiescent" refers, in another embodiment, to a lack of significant replication. In another embodiment, the term refers to a significantly reduced level of replication. In another embodiment, the term refers to a large percentage of cells arrested in the cell cycle. In another embodiment, the cells are arrested at the G1 phase. In another embodiment, the cells are arrested in the G2 phase. In another embodiment, "quiescent" refers to any other art-accepted definition of the term. Each possibility represents a separate embodiment of the present invention.

In one embodiment, embodiment, when the stem cell is a bone marrow-derived human mesenchymal cell, the extracellular matrix (ECM) has an elasticity of about 250 Pa, and comprises a mixture of collagen and fibronectin. In another embodiment, the collagen is rat tail collagen, and the fibronectin is human fibronectin. The ratio of the collagen and fibronectin may vary, and in an embodiment, the ratio of collagen to fibronectin is approximately 5:1. Other ratios of collagen and fibronectin may be used. One of ordinary skill in the art will appreciate that collagen and fibronectin can be obtained from other sources, and that substances other than collagen and fibronectin may be used to present elasticity and bind to integrins on the surface of the cell membrane so that quiescence of the cell is induced.

According to embodiments of the present invention, the extracellular material (ECM) is provided with an appropriate apparent elasticity by coupling the ECM with a substrate such that a stem cell contacting the ECM senses the elasticity of the substrate. Correspondingly, the substrate may be a material whose elasticity, when coupled to the ECM, is sensed by a stem cell contacting the ECM. In some embodiments, the substrate is glass. In other embodiments, the substrate is a gel with elasticity of 250 Pa, or a gel with elasticity of 7500 Pa. These gels may be polyacrylamide gels, and, as known to those with skill in the art, the elasticity of polyacrylamide gels may be varied, for example, by changing the concentrations of acrylamide and bisacrylamide in the gel formulation. The manufacture of gels of varying elasticity that may be used in the method of the present invention will be apparent to one of skill in the art in light of this specification.

The elasticity of the in vivo biological environment of a stem cell may be determined by extracting a sample of physiological tissue from the immediate in vivo environment of the stem cell, and then measuring the shear modulus of that tissue sample. Exemplary procedures for preparing and measuring the elasticity of rat tissue and bovine tissue are described in this specification. Table 1 below provides the elasticity of various types of tissues:

TABLE 1

| Species | Tissue | Elasticity (in Pa) (mean ± SD) |
|---|---|---|
| Bovine | Bone marrow | 220 ± 50 |
| Rat | Subcutaneous fat | 160 ± 70 |
| Rat | Visceral fat | 130 ± 70 |
| Rat | Liver | 403 ± 28 |
| Rat | Skeletal muscle | 2251 ± 166 |

In one embodiment, human MSCs on 250 Pa gels are in a quiescent state awaiting a further signal to determine their fate. In one embodiment, the hMSC's will undergo adipogenic differentiation (induced by chemical factors), or in other embodiments, a return to the cell cycle (induced by coupling the cells to a stiff surface), or osteogenic differentiation (which appears to require both chemical induction and a stiff substrate). Stimulating cells cultured on soft gels with adipogenic differentiation factors results in one embodiment, in a remarkably high number of cells accumulating lipid droplets. In one embodiment, chemical induction is required for osteoblast differentiation. The requirement for synchronized mechanical and chemical stimulation explains in one embodiment, how human MSCs can be compartmentalized into compliant tissues such as bone marrow and yet resist spontaneous differentiation.

Like matrix elasticity, in another embodiment the choice of extracellular ligand strongly affects human MSC adhesion and differentiation. Collagen type 1 is found in a variety of tissues including bone and adipose, and it is regularly used as a substrate for cell adhesion experiments. In one embodiment, on 250 Pa gel, collagen alone does not ensure efficient adhesion of a majority of cells. In one embodiment, a mixture of collagen type I and fibronectin at a ratio of 10:1 provides the best adhesion of cells to the 250 Pa gels without affecting differentiation potential.

Human MSCs have the capacity to remodel their microenvironment by altering the expression of matrix metalloproteases, and this helps in one embodiment to promote efficient differentiation after an initial strong adhesion is achieved.

In one embodiment, DNA synthesis in human MSCs decreases dramatically when human MSCs are cultured on soft gels, developing a round phenotype. This is in contrast with other proliferating cell types such as NIH 3T3 fibroblasts, bovine aortic endothelial cells, and NRK epithelial cells which all continue to divide when cultured on soft gels. Thus, stem cell quiescence on 250 Pa gels is not a general shape-induced failure of cytokinesis, but rather a specific sensitivity of these cells to substrate compliance. Accordingly and in one embodiment, provided herein is a method of maintaining stem cells in a quiescent state, comprising suspending the stem cells in a fibronectin/collagen gel having G' of 250 Pa.

In one embodiment, when nonproliferating human MSCs are presented with a protein gel matrix-coated glass substrate, the cells develop a spindle morphology and reenter the cell cycle. In another embodiment, the presence of a stiff substrate overrides the physical cues from a compliant matrix. In one embodiment, no significant population of cells exhibiting a neuronal phenotype with neurite-like protrusions, are present on soft 250 Pa gels without any chemical induction In one embodiment, substrate elasticity regulates differentiation of cells with specific phenotypes. In another embodiment, mechanical properties alone do not direct stem cell differentiation. This is because several tissues in the body have similar elasticities. For example, brain, fat, and bone marrow tissues all have a storage modulus of approximately 200 Pa, yet all maintain unique populations of cells. In another embodiment, in vivo human MSCs are stored in an individual's bone marrow for decades and yet retain multipotency. In one embodiment, human MSCs are cultured ex vivo on stiff tissue culture plastic and retain multipotency for several passages. In one embodiment, both mechanical and chemical stimuli are integrated by the cell to determine its response. In another embodiment, while chemical stimuli can override the influences of substrate mechanics, in other embodiments, an inappropriate mechanical environment prevents a normal cellular response to chemical agonists. In one embodiment, quiescent cells differentiate into osteoblasts only as a result of changing both their physical and chemical environments to those that stimulate osteogenesis. Accordingly and in one embodiment, a matrix with appropriate elasticity has the capability to maintain a quiescent population of multipotent bone marrow mesenchymal stem cells that respond to both mechanical and chemical stimuli that drive proliferation and differentiation.

Figure 14:
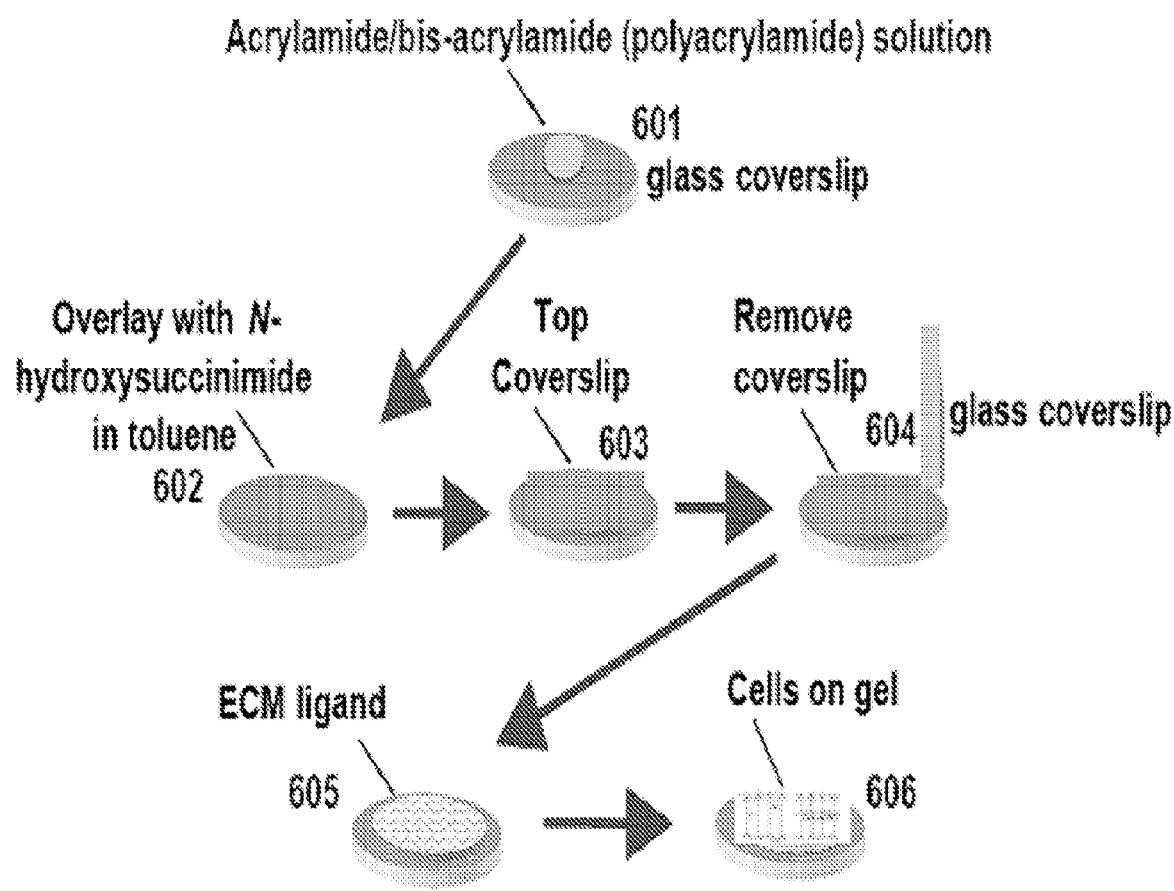
FIG. 14 shows a flow chart for preparing a system for inducing quiescence, differentiation, and proliferation in adult stem cells according to various embodiments of the invention.
Figure 15:
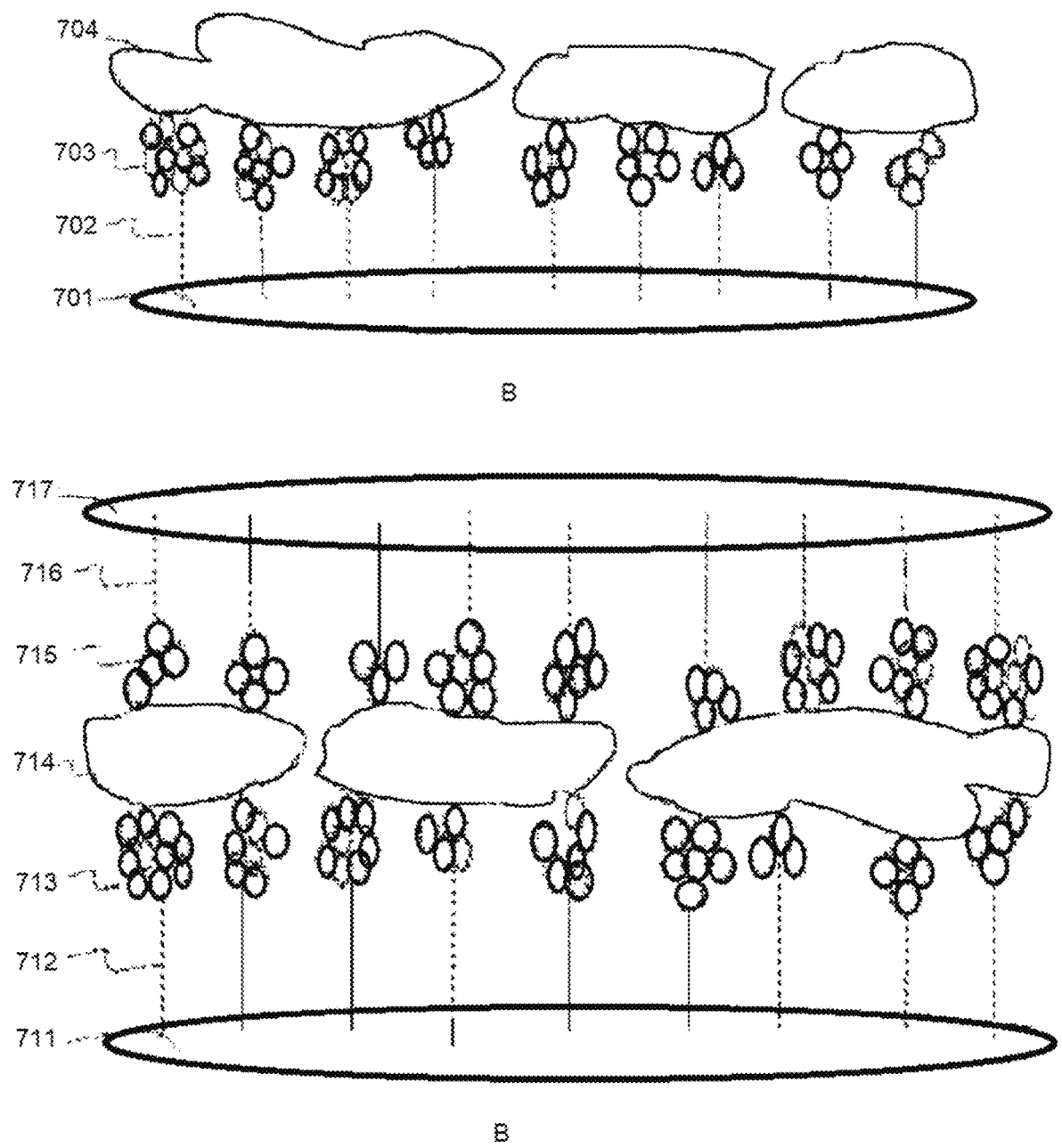
FIG. 15 shows schematic illustrations of embodiments of systems of the present invention.

FIG. 14 illustrates a flow chart for preparing an embodiment of a system for inducing quiescence, differentiation, and proliferation in adult stem cells according to various embodiments of the present invention. Solutions of acrylamide and bisacrylamide are prepared in phosphate buffered saline (PBS) to a total volume of 500 µl. In one embodiment, adjusting the concentration of acrylamide and bisacrylamide enables obtaining a wide range of rigidity. Polymerization is initiated with TEMED (N,N,N',N'-Tetramethylethylenediamine) and ammonium persulfate to form a gel. In step 601, Acrylamide/bisacrylamide (polyacrylamide) solution, a droplet (for example, about 200 µl) of the polymerized gel is deposited on a glass coverslip previously modified with 3-aminopropyltrimethoxysilane and glutaraldehyde. In step 602, overlay with N-hydroxysuccinimide in toluene, approximately 15 µl of 2% acrylic acid N-hydroxysuccinimide ester in toluene is applied to the solution of step 601, and, in stem 603, Top Coverslip, a chlorosilanized coverslip is placed on top of the droplet. In step 604, Remove coverslip, the top coverslip is removed after polymerization is completed and, optionally, the gel is illuminated with ultraviolet light for approximately 10-15 minutes (not shown). In step 605, ECM ligand, N-succinimide acrylate on the top of the gel is reacted with an extracellular matrix ligand, which in an embodiment is a mixture of 0.1 mg/ml of collagen type 1 and 0.02 mg/ml fibronectin. In a further step (not depicted), gels are washed 3 times with PBS and left in PBS until step 606, Cells on gel, when stem cells are seeded on the cells. When bone marrow-derived mesenchymal stem cells are seeded on this material, cells become quiescent even in the presence of chemical stimuli to cause proliferation or differentiation.

Accordingly and in one embodiment, provided herein is a method for inducing or maintaining quiescence and sustaining biological activity in a somatic stem cell ex vivo, comprising: contacting the somatic stem cell with a gel matrix comprising an extracellular material that bind to integrin on the membrane of the somatic stem cell; said gel matrix having a substantially similar elasticity to the elasticity of the predominant in vivo biological microenvironment of the somatic stem cell of the same type in vivo; and providing the somatic stem cell with nutrient material for sustaining biological activity of the somatic stem cell ex vivo.

In a method of the present invention, a stem cell may be contacted with appropriate ECM in various ways. For example, as described in this specification, the ECM may form a layer coupled to the substrate, and the stem cell may be placed on the ECM. Alternatively, the cell may be placed on ECM coupled to the substrate and additionally contacted by ECM placed on the cell, for example by placing on the cell a structure coupling ECM to a substrate that presents the appropriate apparent elasticity to the stem cell.

In another embodiment, there may be two formulations of ECM: a first formulation, which may or may not include nutrient materials, that is coupled to the substrate; and a second formulation that includes nutrient materials and that is not coupled with the substrate. Structures and configurations for contacting stem cells with an appropriate ECM (including substrates and, optionally, linking materials for linking the substrate to the ECM), are described in this specification, including for example FIG. 6, and are apparent to one of skill in the art in light of this specification.

In embodiments of methods of the present invention, a stem cell that is not in a quiescent state is contacted with ECM according to methods of the present invention so that quiescence is induced into the cell and it transitions from a non-quiescent state to a quiescent state. In other embodiments, a quiescent stem cell is contacted with ECM according to methods of the present invention so that quiescence is maintained in the cell and it does not transition from a quiescent state.

Accordingly and in one embodiment, provided herein is a method of modulating development of a mesenchymal stem cell, comprising the step of suspending the mesenchymal stem cell in a gel matrix comprising a gelling agent wherein said gel matrix is coated with a type 1 collagen, a fibronectin, or a combination thereof and wherein said gel matrix is maintained at a predetermined rigidity; and exposing the gel matrix to a growth modulating factor, whereby exposure to the chemical or physical factor results in an increase in the rigidity of the gel matrix to coincide with the rigidity of the ECM in the microenvironment the mesenchymal stem cell is sought to differentiate into In another embodiment, over 80% of the cells are cell cycle arrested. In another embodiment, at least 80% of the cells are cell cycle arrested. In another embodiment, over 70% of the cells are cell cycle arrested. In another embodiment, at least 70% of the cells are cell cycle arrested. In another embodiment, over 75% of the cells are cell cycle arrested. In another embodiment, at least 75% of the cells are cell cycle arrested. In another embodiment, over 82% of the cells are cell cycle arrested. In another embodiment, at least 82% of the cells are cell cycle arrested. In another embodiment, over 85% of the cells are cell cycle arrested. In another embodiment, at least 85% of the cells are cell cycle arrested. In another embodiment, over 87% of the cells are cell cycle arrested. In another embodiment, at least 87% of the cells are cell cycle arrested. In another embodiment, over 90% of the cells are cell cycle arrested. In another embodiment, at least 90% of the cells are cell cycle arrested. In another embodiment, over 92% of the cells are cell cycle arrested. In another embodiment, at least 92% of the cells are cell cycle arrested. In another embodiment, over 93% of the cells are cell cycle arrested. In another embodiment, at least 93% of the cells are cell cycle arrested. In another embodiment, over 94% of the cells are cell cycle arrested. In another embodiment, at least 94% of the cells are cell cycle arrested. In another embodiment, over 95% of the cells are cell cycle arrested. In another embodiment, at least 95% of the cells are cell cycle arrested. In another embodiment, over 96% of the cells are cell cycle arrested. In another embodiment, at least 96% of the cells are cell cycle arrested. In another embodiment, over 97% of the cells are cell cycle arrested. In another embodiment, at least 97% of the cells are cell cycle arrested. In another embodiment, over 98% of the cells are cell cycle arrested. In another embodiment, at least 98% of the cells are cell cycle arrested. In another embodiment, over 99% of the cells are cell cycle arrested. In another embodiment, at least 99% of the cells are cell cycle arrested. Each possibility represents a separate embodiment of the present invention.

In another embodiment, replication is reduced by 50%, relative to replication in a tissue culture dish. In another embodiment, replication is reduced by 60% relative to a tissue culture dish. In another embodiment, replication is reduced by 65% relative to a tissue culture dish. In another embodiment, replication is reduced by 70% relative to a tissue culture dish. In another embodiment, replication is reduced by 75% relative to a tissue culture dish. In another embodiment, replication is reduced by 80% relative to a tissue culture dish. In another embodiment, replication is reduced by 85% relative to a tissue culture dish. In another embodiment, replication is reduced by 90% relative to a tissue culture dish. In another embodiment, replication is reduced by 95% relative to a tissue culture dish. In another embodiment, replication is reduced by 97% relative to a tissue culture dish. In another embodiment, replication is reduced by over 97% relative to a tissue culture dish. In another embodiment, replication is reduced by over 98% relative to a tissue culture dish. In another embodiment, replication is reduced by over 99% relative to a tissue culture dish. Each possibility represents a separate embodiment of the present invention.

In another embodiment, a method of the present invention further comprises the step of subsequently (e.g. following culturing in the presence of a gel or matrix of the present invention) plating the mesenchymal stem cell population in a tissue-culture apparatus. In another embodiment, the tissue culture apparatus contains induction medium. In another embodiment, the step of subsequently plating is performed with chemical induction. Each possibility represents a separate embodiment of the present invention.

In another embodiment, provided herein is a method of studying proliferation or differentiation of a mesenchymal stem cell, comprising the step of culturing the mesenchymal stem cell in a gel or matrix with a rigidity in a range of 150-750 Pa, thereby studying proliferation or differentiation of a mesenchymal stem cell.

The adipocyte population of methods and compositions of the present invention is, in another embodiment, a population comprising adipocytes. In another embodiment, the population is enriched for adipocytes. In another embodiment, the population is a partially purified adipocytes population. In another embodiment, the adipocytes are isolated from a biological source, followed by a purification or enrichment step. In another embodiment, isolation from the biological source is followed by culturing. In another embodiment, isolation from the biological source is followed by culturing and a purification or enrichment step. Each possibility represents a separate embodiment of the present invention.

In another embodiment, the cell population of methods and compositions of the present invention is cultured in the presence of a gel or matrix of methods and compositions of the present invention. In another embodiment, the cell population is cultured in the gel or matrix. In another embodiment, the cell population is cultured on the gel or matrix. In another embodiment, the cell population is cultured in a tissue culture apparatus containing the gel or matrix. Each possibility represents a separate embodiment of the present invention.

"Mesenchymal stem cell population" refers, in another embodiment, to a population comprising mesenchymal stem cells (MSC). In another embodiment, the population is enriched for MSC. In another embodiment, the population is a partially purified MSC population. In another embodiment, the MSC are isolated from a biological source, followed by a purification or enrichment step. In another embodiment, isolation from the biological source is followed by culturing. In another embodiment, isolation from the biological source is followed by culturing and a purification or enrichment step. Each possibility represents a separate embodiment of the present invention.

"Mesenchymal" cells of methods and compositions of the present invention are isolated or purified, in another embodiment, from bone marrow. In another embodiment, the cells are bone marrow-derived mesenchymal stem cell. In another embodiment, the cells are isolated or purified from adipose tissue. In another embodiment, the cells are isolated or purified from cartilage. In another embodiment, the cells are isolated or purified from any other tissue known in the art. Each possibility represents a separate embodiment of the present invention.

In another embodiment, a gel or matrix of methods and compositions of the present invention has a stiffness of 150-750 pascals (Pa). In another embodiment, a gel or matrix of methods and compositions of the present invention has a shear modulus of 150-750 Pa. Each possibility represents a separate embodiment of the present invention.

In another embodiment, a gel or matrix of methods and compositions of the present invention has a stiffness equivalent to a biological tissue. In another embodiment, the biological tissue is bone marrow. In another embodiment, the biological tissue is fat tissue. In another embodiment, the biological tissue is any other biological tissue known in the art. Each possibility represents a separate embodiment of the present invention.

In one embodiment, the gel matrix described herein are capable of forming gels of various strength, depending on their structure and concentration as well as, in another embodiment, environmental factors such as ionic strength, pH and temperature. The combined viscosity and gel behavior referred to as "viscoelasticity" in one embodiment, are examined by determining the effect that an oscillating force has on the movement of the material. In another embodiment elastic modulus (G'), viscous modulus (G"), and complex viscosity ($\eta^*$) are the parameters sought to be changed using the methods described herein, and these are analyzed in another embodiment by varying either stress or strain harmonically with time (Table 1). These parameters are derived from the complex modulus (G*), which is the ratio of maximum stress to maximum strain, and the phase angle ($\delta$), which is the angle that the stress and strain are out of phase.

TABLE 2

Relationships between dynamic moduli, phase angle ($\delta$), and frequency ($\omega$).

| Term | Symbol | Definition | Information provided |
|---|---|---|---|
| Complex modulus | G* | $[(G')^2 + (G'')^2]^{0.5}$ | All viscoelastic characteristics |
| Elastic modulus, storage modulus | G' | G* cos $\delta$ | Energy stored per deformation cycle; solid-like or elastic behavior |
| Viscous modulus, loss modulus | G" | G* sin $\delta$ | Energy dissipated per deformation cycle; gluid-like or viscous behavior |
| Complex viscosity | $\eta^*$ | G*/$\omega$ | Viscoelastic flow |

In one embodiment, in the gel matrices described herein, some of the deformation caused by shear stress is elastic and will return to zero when the force is removed. The remaining deformation such as that deformation created by the sliding displacement of the chains through the solvent in one embodiment will not return to zero when the force is removed. Under a constant force the elastic displacement remains constant in one embodiment, whereas the sliding displacement continues, so increasing.

In one embodiment, the term "elastic," or "elasticity," and like terms refer to a physical property of the gel matrices described herein, namely the deformability of the gel under mechanical force and the ability of the gel matrix to retain its original shape when the deforming force is removed. In another embodiment, the term "elastic modulus" refers to Young's Modulus and is a measure of the ratio of (a) the uniaxial stress along an axis of the material to (b) the accompanying normal strain along that axis.

The shear modulus (resulting from changing strain) is the ratio of the shear stress to the shear strain. It follows from the complex relationship similar to the above that:

$$G^* = G' + iG''$$

where G* is the complex shear modulus, G' is the in-phase storage modulus, i is a material-related factor and G" is the out-of-phase similarly-directed loss modulus; G*=E(G'2+G"2). The frequency where these parameters cross over corresponds to a relaxation time ($\tau$) specific for the material.

In one embodiment, linear viscoelastic properties of the gel matrices described herein are determined by measurements in an oscillating shear flow at small amplitude and with variable angular frequency. The values for G' and G" are determined to a great extent here by the concentration of the cellulose derivatives in the aqueous solution and the magnitude of the representative viscosity value. Therefore, hereinafter, only the relative course of G' and G" with increasing angular frequency $\omega$, is considered. In another embodiment, at a concentration of 1.5 to 2% (w/w) of cellulose derivative of aqueous solution and a temperature of approximately 20° C., the behavior of G' and G" for the cellulose derivatives is such that at a low angular frequency ($\omega$, the storage modulus G' is less than the loss modulus G", but with increasing angular frequency G' increases more greatly than G". In another embodiment, G', above a certain angular frequency, finally becomes greater than G", and the solution at high values of angular frequency thus predominantly reacts elastically. This behavior is attenuated or changed using the modulating methods described herein.

In another embodiment, the term "Elasticity" refers to the physical property of a material that defines its ability to deform by stress, whether or not the deformation is reversible. As used in this specification, elasticity and rigidity are inversely related, and the elasticity (rigidity) of a material may be measured by using an RFS III fluids spectrometer rheometer, available from Rheometrics, Piscataway, N.J., using a 2% oscillatory shear strain at a frequency of 10 radians per second. Elasticity and other 10 rheological properties of cells and other physiological tissues can be measured using any of a variety of methods known to those skilled in the art. Such methods may involve the use of rheometers or atomic force microscopes, as examples. (See, e.g., Engler A J, Rehfeldt F, Sen S, Discher D E, "Microtissue elasticity: measurements by atomic force microscopy and its influence on cell differentiation," Methods Cell Biol. 2007; 83:521-45; 15 Yeung T, Georges P C, Flanagan L A, Marg B, Ortiz M, Funaki M, Zahir N, Ming W, Weaver V, Janmey P A, "Effects of substrate stiffness on cell morphology, cytoskeletal structure, and adhesion," Cell Motil Cytoskeleton. 2005 January; 60(1):24-34.).

In one embodiment, the term "Intrinsic viscosity ($[\eta^*]$) refers to the limit of the reduced viscosity extrapolated to zero concentration. As with the reduced viscosity, it has units of reciprocal concentration, for example, mL g$^{-1}$.

In one embodiment, rigidity or stiffness, refers to the G' values observed or measured.

In another embodiment, a gel or matrix of methods and compositions of the present invention is coated with a solution comprising an adhesion protein. In another embodiment, the adhesion protein is a collagen. In another embodiment, the adhesion protein is a type 1 collagen. In another embodiment, the adhesion protein is a fibronectin. In another embodiment, the adhesion protein is any other adhesion protein known in the art. In another embodiment, the gel or matrix is coating with a solution comprising a combination of adhesion proteins. In another embodiment, the gel or matrix is coating with a solution comprising a collagen and a fibronectin. In another embodiment, the gel or matrix is coating with a solution comprising a type I collagen and a fibronectin. Each possibility represents a separate embodiment of the present invention.

In another embodiment, the collagen of methods and compositions of the present invention is a recombinant collagen. In another embodiment, the collagen is purified from a biological source. In another embodiment, the collagen is a type 1 collagen. In another embodiment, the collagen is any other type of collagen known in the art. Each possibility represents a separate embodiment of the present invention.

In another embodiment, the fibronectin of methods and compositions of the present invention is a recombinant fibronectin. In another embodiment, the fibronectin is purified from a biological source. In another embodiment, the fibronectin is a type 1 fibronectin. In another embodiment, the fibronectin is any other type of fibronectin known in the art. Each possibility represents a separate embodiment of the present invention.

The gelling agent of methods and compositions of the present invention is, in another embodiment, an acrylamide. In another embodiment, the gelling agent is an acrylamide-bisacrylamide mixture. In another embodiment, the gelling agent comprises acrylamide. In another embodiment, the gelling agent comprises an acrylamide-bisacrylamide mixture. Each possibility represents a separate embodiment of the present invention.

In another embodiment, an acrylamide gel of methods and compositions of the present invention has an acrylamide:bisacrylamide ratio of between 100:1 and 30:1. In another embodiment, the acrylamide gel is prepared from a solution having an acrylamide:bisacrylamide ratio of between 100:1 and 30:1. In another embodiment, the ratio is between 100:1 and 20:1. In another embodiment, the acrylamide:bisacrylamide ratio is between 100:1 and 40:1. In another embodiment, the ratio is between 100:1 and 50:1. In another embodiment, the ratio is between 100:1 and 60:1. In another embodiment, the ratio is between 100:1 and 70:1. In another embodiment, the ratio is between 120:1 and 30:1. In another embodiment, the ratio is between 120:1 and 40:1. In another embodiment, the ratio is between 120:1 and 50:1. In another embodiment, the ratio is between 120:1 and 60:1. In another embodiment, the ratio is between 120:1 and 70:1. In another embodiment, the ratio is between 90:1 and 20:1. In another embodiment, the ratio is between 90:1 and 30:1. In another embodiment, the ratio is between 90:1 and 40:1. In another embodiment, the ratio is between 90:1 and 50:1. In another embodiment, the ratio is between 90:1 and 60:1. In another embodiment, the ratio is between 80:1 and 20:1. In another embodiment, the ratio is between 80:1 and 30:1. In another embodiment, the ratio is between 80:1 and 40:1. In another embodiment, the ratio is between 80:1 and 50:1.

In another embodiment, the ratio is 30:1. In another embodiment, the ratio is 20:1. In another embodiment, the ratio is 25:1. In another embodiment, the ratio is 35:1. In another embodiment, the ratio is 40:1. In another embodiment, the ratio is 45:1. In another embodiment, the ratio is 50:1. In another embodiment, the ratio is 55:1. In another embodiment, the ratio is 60:1. In another embodiment, the ratio is 65:1. In another embodiment, the ratio is 70:1. In another embodiment, the ratio is 75:1. In another embodiment, the ratio is 80:1. In another embodiment, the ratio is 85:1. In another embodiment, the ratio is 90:1. In another embodiment, the ratio is 95:1. In another embodiment, the ratio is 100:1.

Each acrylamide:bisacrylamide ratio represents a separate embodiment of the present invention.

In another embodiment, an acrylamide gel of methods and compositions of the present invention has a total acrylamide concentration of 3-5%. In another embodiment, the acrylamide gel is prepared from a solution having a total acrylamide concentration of 3-5%. In another embodiment, the total acrylamide concentration is 2%. In another embodiment, the concentration is 2.5%. In another embodiment, the concentration is 3%. In another embodiment, the concentration is 3.5%. In another embodiment, the concentration is 4%. In another embodiment, the concentration is 4.5%. In another embodiment, the concentration is 5%. In another embodiment, the concentration is 5.5%. In another embodiment, the concentration is 6%. In another embodiment, the concentration is 2-5%. In another embodiment, the concentration is 2.5-5%. In another embodiment, the concentration is 3.5-5%. In another embodiment, the concentration is 2-4%. In another embodiment, the concentration is 2-4.5%. In another embodiment, the concentration is 2-5%. Each possibility represents a separate embodiment of the present invention.

In another embodiment, the gelling agent of methods and compositions of the present invention is a fibrin protein. In another embodiment, the gelling agent is a fibrinogen protein. In another embodiment, the fibrinogen is depleted of clotting factors. Each possibility represents a separate embodiment of the present invention.

In another embodiment, the concentration of the recombinant fibrin or fibrinogen protein in a gel or matrix of methods and compositions of the present invention is 3-10 mg/mL. In another embodiment, the concentration is 3-12 mg/mL. In another embodiment, the concentration is 3-9 mg/mL. In another embodiment, the concentration is 3-8 mg/mL. In another embodiment, the concentration is 3-7 mg/mL. In another embodiment, the concentration is 3-6 mg/mL. In another embodiment, the concentration is 2-12 mg/mL. In another embodiment, the concentration is 2-10 mg/mL. In another embodiment, the concentration is 2-9 mg/mL. In another embodiment, the concentration is 2-8 mg/mL. In another embodiment, the concentration is 2-7 mg/mL. In another embodiment, the concentration is 2-6 mg/mL. In another embodiment, the concentration is 4-12 mg/mL. In another embodiment, the concentration is 4-10 mg/mL. In another embodiment, the concentration is 4-9 mg/mL. In another embodiment, the concentration is 4-8 mg/mL. In another embodiment, the concentration is 4-7 mg/mL. In another embodiment, the concentration is 5-12 mg/mL. In another embodiment, the concentration is 5-10 mg/mL. In another embodiment, the concentration is 5-9 mg/mL. In another embodiment, the concentration is 5-8 mg/mL. In another embodiment, the concentration is 2 mg/mL. In another embodiment, the concentration is 2.5 mg/mL. In another embodiment, the concentration is 3 mg/mL. In another embodiment, the concentration is 3.5 mg/mL. In another embodiment, the concentration is 4 mg/mL. In another embodiment, the concentration is 4.5 mg/mL. In another embodiment, the concentration is 5 mg/mL. In another embodiment, the concentration is 6 mg/mL. In another embodiment, the concentration is 7 mg/mL. In another embodiment, the concentration is 8 mg/mL. In another embodiment, the concentration is 9 mg/mL. In another embodiment, the concentration is 10 mg/mL. In another embodiment, the concentration is 11 mg/mL. In another embodiment, the concentration is 12 mg/mL. Each possibility represents a separate embodiment of the present invention.

In another embodiment, a fibrin or fibrinogen protein of methods and compositions of the present invention is a fibrin or fibrinogen protein of a heterothermic animal. In another embodiment, the fibrin or fibrinogen protein is a fibrin or fibrinogen protein of a homeothermic animal. In another embodiment, the fibrin or fibrinogen is from a fish. In another embodiment, the fibrin or fibrinogen is from a salmon. In another embodiment, the fibrin or fibrinogen is from any other fish known in the art. In another embodiment, the fibrin or fibrinogen is from any other heterothermic known in the art. In another embodiment, the fibrin or fibrinogen is from a mammal. In another embodiment, the fibrin or fibrinogen is human fibrin or fibrinogen. In another embodiment, the fibrin or fibrinogen is bovine fibrin or fibrinogen. In another embodiment, the fibrin or fibrinogen is from any other mammal known in the art. In another embodiment, the fibrin or fibrinogen is from any other homoeothermic known in the art. Each possibility represents a separate embodiment of the present invention.

In another embodiment, the gelling agent is agarose. In another embodiment, the gelling agent is agar. In another embodiment, the gelling agent is a glycosaminoglycan. In another embodiment, the gelling agent is a collagen. In another embodiment, the gelling agent is carrageen. In another embodiment, the gelling agent is carrageenan. In another embodiment, the gelling agent is locust bean gum. In another embodiment, the gelling agent is glycerine. In another embodiment, the gelling agent of methods and compositions of the present invention is any other gelling agent known in the art. Each possibility represents a separate embodiment of the present invention.

The gel or matrix of methods and compositions of the present invention is, in another embodiment, a 2-dimensional gel or matrix. In another embodiment, the gel or matrix is a 3-dimensional gel or matrix. In another embodiment, the gel or matrix is any other type of gel or matrix known in the art. Each possibility represents a separate embodiment of the present invention.

In another embodiment, a gel or matrix of methods and compositions of the present invention further comprises an animal serum. In another embodiment, the animal serum is a fetal bovine serum. In another embodiment, the animal serum is a bovine calf serum. In another embodiment, the animal serum is a horse serum. In another embodiment, the animal serum is any other type of growth factor-containing animal serum known in the art. Each possibility represents a separate embodiment of the present invention.

In another embodiment, a gel or matrix of methods and compositions of the present invention further comprises a protease inhibitor.

In another embodiment, a protease inhibitor of methods and compositions of the present invention inhibits the function of a peptidase. In another embodiment, the protease inhibitor is a protein. In some embodiments, the protease inhibitor is a cysteine protease inhibitor, a serine protease inhibitor (serpin), a trypsin inhibitor, a threonine protease inhibitor, an aspartic protease inhibitor, or a metallo-protease inhibitor. In another embodiment, a protease inhibitor is a suicide inhibitor, a transition state inhibitor, or a chelating agent.

In another embodiment, the protease inhibitor is soybean trypsin inhibitor (SBTI). In another embodiment, the protease inhibitor is AEBSF-HCl. In another embodiment, the inhibitor is (epsilon)-aminocaproic acid. In another embodiment, the inhibitor is (alpha) 1-antichymotypsin. In another embodiment, the inhibitor is antithrombin III. In another embodiment, the inhibitor is (alpha) 1-antitrypsin ([alpha] 1-proteinase inhibitor). In another embodiment, the inhibitor is APMSF-HCl (4-amidinophenyl-methane sulfonyl-fluoride). In another embodiment, the inhibitor is aprotinin. In another embodiment, the inhibitor is benzamidine-HCl. In another embodiment, the inhibitor is chymostatin. In another embodiment, the inhibitor is DFP (diisopropylfluoro-phosphate). In another embodiment, the inhibitor is leupeptin. In another embodiment, the inhibitor is PEFABLOC® SC (4-(2-Aminoethyl)-benzenesulfonyl fluoride hydrochloride). In another embodiment, the inhibitor is PMSF (phenylmethyl sulfonyl fluoride). In another embodiment, the inhibitor is TLCK (1-Chloro-3-tosylamido-7-amino-2-heptanone HCl). In another embodiment, the inhibitor is TPCK (1-Chloro-3-tosylamido-4-phenyl-2-butanone). In another embodiment, the inhibitor is trypsin inhibitor from egg white (Ovomucoid). In another embodiment, the inhibitor is trypsin inhibitor from soybean. In another embodiment, the inhibitor is aprotinin. In another embodiment, the inhibitor is pentamidine isethionate. In another embodiment, the inhibitor is pepstatin. In another embodiment, the inhibitor is guanidium. In another embodiment, the inhibitor is alpha2-macroglobulin. In another embodiment, the inhibitor is a chelating agent of zinc. In another embodiment, the inhibitor is iodoacetate. In another embodiment, the inhibitor is zinc. Each possibility represents a separate embodiment of the present invention.

In another embodiment, the amount of protease inhibitor utilized in methods and compositions of the present invention is 0.1 mg/liter. In another embodiment, the amount of protease inhibitor is 0.2 mg/liter. In another embodiment, the amount is 0.3 mg/liter. In another embodiment, the amount is 0.4 mg/liter. In another embodiment, the amount is 0.6 mg/liter. In another embodiment, the amount is 0.8 mg/liter. In another embodiment, the amount is 1 mg/liter. In another embodiment, the amount is 1.5 mg/liter. In another embodiment, the amount is 2 mg/liter. In another embodiment, the amount is 2.5 mg/liter. In another embodiment, the amount is 3 mg/liter. In another embodiment, the amount is 5 mg/liter. In another embodiment, the amount is 7 mg/liter. In another embodiment, the amount is 10 mg/liter. In another embodiment, the amount is 12 mg/liter. In another embodiment, the amount is 15 mg/liter. In another embodiment, the amount is 20 mg/liter. In another embodiment, the amount is 30 mg/liter. In another embodiment, the amount is 50 mg/liter. In another embodiment, the amount is 70 mg/liter. In another embodiment, the amount is 100 mg/liter.

In another embodiment, the amount of protease inhibitor is 0.1-1 mg/liter. In another embodiment, the amount of protease inhibitor is 0.2-1 mg/liter. In another embodiment, the amount is 0.3-1 mg/liter. In another embodiment, the amount is 0.5-1 mg/liter. In another embodiment, the amount is 0.1-2 mg/liter. In another embodiment, the amount is 0.2-2 mg/liter. In another embodiment, the amount is 0.3-2 mg/liter. In another embodiment, the amount is 0.5-2 mg/liter. In another embodiment, the amount is 1-2 mg/liter. In another embodiment, the amount is 1-10 mg/liter. In another embodiment, the amount is 2-10 mg/liter. In another embodiment, the amount is 3-10 mg/liter. In another embodiment, the amount is 5-10 mg/liter. In another embodiment, the amount is 1-20 mg/liter. In another embodiment, the amount is 2-20 mg/liter. In another embodiment, the amount is 3-20 mg/liter. In another embodiment, the amount is 5-20 mg/liter. In another embodiment, the amount is 10-20 mg/liter. In another embodiment, the amount is 10-100 mg/liter. In another embodiment, the amount is 20-100 mg/liter. In another embodiment, the amount is 30-100 mg/liter. In another embodiment, the amount is 50-100 mg/liter. In another embodiment, the amount is 10-200 mg/liter. In another embodiment, the amount is 20-200 mg/liter. In another embodiment, the amount is 30-200 mg/liter. In another embodiment, the amount is 50-200 mg/liter. In another embodiment, the amount is 100-200 mg/liter.

In another embodiment, the amount of protease inhibitor utilized in methods and compositions of the present invention is 1000 k.i.u. (kallikrein inactivator units)/liter. In another embodiment, the amount is 10 k.i.u./liter. In another embodiment, the amount is 12 k.i.u./liter. In another embodiment, the amount is 15 k.i.u./liter. In another embodiment, the amount is 20 k.i.u./liter. In another embodiment, the amount is 30 k.i.u./liter. In another embodiment, the amount is 40 k.i.u./liter. In another embodiment, the amount is 50 k.i.u./liter. In another embodiment, the amount is 70 k.i.u./liter. In another embodiment, the amount is 100 k.i.u./liter. In another embodiment, the amount is 150 k.i.u./liter. In another embodiment, the amount is 200 k.i.u./liter. In another embodiment, the amount is 300 k.i.u./liter. In another embodiment, the amount is 500 k.i.u./liter. In another embodiment, the amount is 700 k.i.u./liter. In another embodiment, the amount is 1500 k.i.u./liter. In another embodiment, the amount is 3000 k.i.u./liter. In another embodiment, the amount is 4000 k.i.u./liter. In another embodiment, the amount is 5000 k.i.u./liter.

Each amount of protease inhibitor represents a separate embodiment of the present invention.

In another embodiment, the protease targeted by the protease inhibitor of methods and compositions of the present invention is a serine protease. In another embodiment, the protease is trypsin. In another embodiment, the protease is chymotrypsin. In another embodiment, the protease is carboxypeptidase. In another embodiment, the protease is aminopeptidase. In another embodiment, the protease is any other protease that functions in the duodenum or the small intestine. Each possibility represents a separate embodiment of the present invention.

The mesenchymal stem cell population of methods and compositions of the present invention is, in another embodiment, an adult mesenchymal stem cell population. In another embodiment, the mesenchymal stem cell population is a juvenile mesenchymal stem cell population. In another embodiment, the mesenchymal stem cell population is an infantile mesenchymal stem cell population. In another embodiment, the mesenchymal stem cell population is a fetal mesenchymal stem cell population. In another embodiment, the mesenchymal stem cell population is a human mesenchymal stem cell population. In another embodiment, the mesenchymal stem cell population is from any animal known in the art. Each possibility represents a separate embodiment of the present invention.

In another embodiment, the cell type of interest is a stem cell. In another embodiment, the cell type of interest is a haematopoietic stem cell. In another embodiment, the cell type of interest is an adipocyte. In another embodiment, the cell type of interest is an endothelial progenitor cell. In another embodiment, the cell type of interest is a neural stem cell. In another embodiment, the cell type of interest is an adult tissue-residing progenitor cell. In another embodiment, the cell type of interest is an adult tissue-residing pancreatic progenitor cell. In another embodiment, the cell type of interest is a regenerating native beta-cell. In another embodiment, the cell type of interest is a gastrointestinal stem cell. In another embodiment, the cell type of interest is a hepatopancreatic epithelial stem cell. In another embodiment, the cell type of interest is an epidermal stem cell. In another embodiment, the cell type of interest is an intestinal epithelial stem cell. In another embodiment, the cell type of interest is a retinal stem cell. In another embodiment, the cell type of interest is a neuronal epithelial stem cell. In another embodiment, the cell type of interest is a muscle stem cell. In another embodiment, the cell type of interest is an endothelial stem cell. In another embodiment, the cell type of interest is a peripheral blood stem cell. In another embodiment, the cell type of interest is any other type of stem cell known in the art.

In another embodiment, the cell type of interest is a progenitor cell. In another embodiment, the cell type of interest is a chrondrogenic progenitor cell. In another embodiment, the cell type of interest is an adipogenic progenitor cell. In another embodiment, the cell type of interest is a marrow stroma progenitor cell. In another embodiment, the cell type of interest is a myogenic progenitor cell. In another embodiment, the cell type of interest is an osteogenic progenitor cell. In another embodiment, the cell type of interest is a tendon progenitor cell. In another embodiment, the cell type of interest is any other type of progenitor cell known in the art.

In another embodiment, the cell type of interest is a progeny cell type. In another embodiment, the cell type of interest is a chondrocyte. In another embodiment, the cell type of interest is a stromal cell. In another embodiment, the cell type of interest is a myotube cell. In another embodiment, the cell type of interest is an osteocyte. In another embodiment, the cell type of interest is a tenocyte. In another embodiment, the cell type of interest is any other progeny cell type known in the art.

In another embodiment, a method of the present invention further comprises the step of incubating the mesenchymal stem cells in an induction medium. In another embodiment, the induction medium is a stem cell induction medium. In another embodiment, the induction medium is an osteoblast induction medium. In another embodiment, the induction medium is a haematopoietic stem cell induction medium. In another embodiment, the induction medium is an adipocyte induction medium. In another embodiment, the induction medium is an endothelial progenitor cell induction medium. In another embodiment, the induction medium is a neural stem cell induction medium. In another embodiment, the induction medium is an adult tissue-residing progenitor cell induction medium. In another embodiment, the induction medium is an adult tissue-residing pancreatic progenitor cell induction medium. In another embodiment, the induction medium is a regenerating native beta-cell induction medium. In another embodiment, the induction medium is a gastrointestinal stem cell induction medium. In another embodiment, the induction medium is a hepatopancreatic epithelial stem cell induction medium. In another embodiment, the induction medium is an epidermal stem cell induction medium. In another embodiment, the induction medium is an intestinal epithelial stem cell induction medium. In another embodiment, the induction medium is a retinal stem cell induction medium. In another embodiment, the induction medium is a neuronal epithelial stem cell induction medium. In another embodiment, the induction medium is a muscle stem cell induction medium. In another embodiment, the induction medium is an endothelial stem cell induction medium. In another embodiment, the induction medium is a peripheral blood stem cell induction medium. In another embodiment, the induction medium is any other type of induction medium known in the art.

In another embodiment, the induction medium is a progenitor cell induction medium. In another embodiment, the induction medium is a chrondrogenic progenitor cell induction medium. In another embodiment, the induction medium is an adipogenic progenitor cell induction medium. In another embodiment, the induction medium is a marrow stroma progenitor cell induction medium. In another embodiment, the induction medium is a myogenic progenitor cell induction medium. In another embodiment, the induction medium is an osteogenic progenitor cell induction medium. In another embodiment, the induction medium is a tendon progenitor cell induction medium. In another embodiment, the induction medium is any other type of progenitor cell known in the art.

In another embodiment, the induction medium is any other type of induction medium known in the art. Each possibility represents a separate embodiment of the present invention.

The step of culturing of methods and compositions of the present invention is performed, in another embodiment, for at least 5 days. In another embodiment, the step of culturing is performed for at least 4 days. In another embodiment, the step of culturing is performed for at least 6 days. In another embodiment, the step of culturing is performed for at least 7 days. In another embodiment, the step of culturing is performed for at least 8 days. In another embodiment, the step of culturing is performed for at least 10 days. In another embodiment, the step of culturing is performed for at least 12 days. In another embodiment, the step of culturing is performed for at least 15 days. In another embodiment, the step of culturing is performed for at least 20 days. In another embodiment, the step of culturing is performed for at least 25 days. In another embodiment, the step of culturing is performed for at least 30 days. In another embodiment, the step of culturing is performed for at least 35 days. In another embodiment, the step of culturing is performed for at least 40 days. In another embodiment, the step of culturing is performed for at least 50 days. In another embodiment, the step of culturing is performed for at least 60 days. In another embodiment, the step of culturing is performed for over 4 days. In another embodiment, the step of culturing is performed for over 6 days. In another embodiment, the step of culturing is performed for over 7 days. In another embodiment, the step of culturing is performed for over 8 days. In another embodiment, the step of culturing is performed for over 10 days. In another embodiment, the step of culturing is performed for over 12 days. In another embodiment, the step of culturing is performed for over 15 days. In another embodiment, the step of culturing is performed for over 20 days. In another embodiment, the step of culturing is performed for over 25 days. In another embodiment, the step of culturing is performed for over 30 days. In another embodiment, the step of culturing is performed for over 35 days. In another embodiment, the step of culturing is performed for over 40 days. In another embodiment, the step of culturing is performed for over 50 days. In another embodiment, the step of culturing is performed for over 60 days. In another embodiment, the step of culturing is performed for 4 days. In another embodiment, the step of culturing is performed for 6 days. In another embodiment, the step of culturing is performed for 7 days. In another embodiment, the step of culturing is performed for 8 days. In another embodiment, the step of culturing is performed for 10 days. In another embodiment, the step of culturing is performed for 12 days. In another embodiment, the step of culturing is performed for 15 days. In another embodiment, the step of culturing is performed for 20 days. In another embodiment, the step of culturing is performed for 25 days. In another embodiment, the step of culturing is performed for 30 days. In another embodiment, the step of culturing is performed for 35 days. In another embodiment, the step of culturing is performed for 40 days. In another embodiment, the step of culturing is performed for 50 days. In another embodiment, the step of culturing is performed for 60 days. In another embodiment, the step of culturing is performed for at over 60 days. Each possibility represents a separate embodiment of the present invention.

In another embodiment, the step of culturing the mesenchymal stem cell population in a gel or matrix of the present invention is preceded by a step of culturing the mesenchymal stem cells in a tissue culture apparatus. In another embodiment, the tissue culture apparatus is a dish. In another embodiment, the tissue culture apparatus is a plate. In another embodiment, the tissue culture apparatus is a flask. In another embodiment, the tissue culture apparatus is a bottle. In another embodiment, the tissue culture apparatus is a tube. In another embodiment, the tissue culture apparatus is any other type of tissue culture apparatus known in the art. In another embodiment, the step of culturing is preceded by a step of culturing the mesenchymal stem cells in tissue-culture media; e.g. not in the presence of a gel or matrix of the present invention. In another embodiment, the step of culturing the cells in a tissue culture apparatus or in tissue culture media is performed after isolation of the mesenchymal stem cell population from a biological sample. In another embodiment, the step of culturing is performed after purification of the mesenchymal stem cell population from a biological sample. In another embodiment, the step of culturing is performed after enrichment of the mesenchymal stem cell population in a biological sample. Each possibility represents a separate embodiment of the present invention.

In another embodiment, the step of culturing the mesenchymal stem cell population in a gel or matrix of the present invention is performed directly after isolation of the mesenchymal stem cell population from a biological sample. In another embodiment, the step of culturing is performed directly after purification of the mesenchymal stem cell population from a biological sample. In another embodiment, the step of culturing is performed directly after enrichment of the mesenchymal stem cell population in a biological sample. "Directly" refers, in another embodiment, to a culturing step in the absence of culturing first in a tissue culture apparatus. Each possibility represents a separate embodiment of the present invention.

The progenitor cell population of methods and compositions of the present invention is, in another embodiment, a hematopoietic stem cell population. In another embodiment, the progenitor cell population is an endothelial cell precursor population. In another embodiment, the progenitor cell population is a satellite cell population (e.g. muscle cell precursors). In another embodiment, the progenitor cell population is a population of transit-amplifying neural progenitors of the rostral migratory stream. In another embodiment, the progenitor cell population is a bone marrow stromal cell population. In another embodiment, the progenitor cell population is any other progenitor cell population known in the art. Each possibility represents a separate embodiment of the present invention.

"Progenitor cell population" refers, in another embodiment, to a population comprising progenitor cells. In another embodiment, the population is enriched for progenitor cells. In another embodiment, the population is a partially purified progenitor cell population. In another embodiment, the progenitor cells are isolated from a biological source, followed by a purification or enrichment step. In another embodiment, isolation from the biological source is followed by culturing. In another embodiment, isolation from the biological source is followed by culturing and a purification or enrichment step. Each possibility represents a separate embodiment of the present invention.

In another embodiment, provided herein is a method of differentiating a transformed cell into a differentiated cell type, comprising the step of culturing the transformed cell in a gel or matrix of the present invention, thereby differentiating a transformed cell into a differentiated cell type. In another embodiment, the differentiated cell type is a progenitor cell. In another embodiment, the differentiated cell type is a progeny cell type. In another embodiment, the differentiated cell type is a tissue cell type. In another embodiment, the differentiated cell type is one of the above cell types. In another embodiment, the differentiated cell type is any other type of differentiated cell type known in the art. Each possibility represents a separate embodiment of the present invention.

In another embodiment, a cell or cell population prepared by a method of the present invention is used for replacement of damaged tissues in a subject. In another embodiment, a cell or cell population prepared by a method of the present invention is used as carrier for anti-cancer agents (Kassem M, Ann N Y Acad. Sci. 2006 May; 1067:436-42). Each possibility represents a separate embodiment of the present invention.

Methods for determining proliferative capacity and differentiation potency of mesenchymal stem cells are well known in the art, and are described, for example, in Baxter M A et al (Study of telomere length reveals rapid aging of human marrow stromal cells following in vitro expansion. Stem Cells. 2004; 22(5):675-82), Liu L et al (Telomerase deficiency impairs differentiation of mesenchymal stem cells. Exp Cell Res. 2004 Mar. 10; 294(1):1-8), and Bonab M M et al (Aging of mesenchymal stem cell in vitro. BMC Cell Biol. 2006 Mar. 10; 7:14). Each possibility represents another embodiment of the present invention.

In another embodiment, an advantage of methods and compositions of the present invention is the lack of immortalization of mesenchymal stem cells. In another embodiment, an advantage is lack of evolution of cancer cells from a mesenchymal stem cell population. In another embodiment, an advantage is retention of ability of the target cells to differentiate into multiple cell types. In another embodiment, an advantage is retention of proliferative capacity of the cells. In another embodiment, an advantage is retention of ability of the cells to support hematopoietic cell growth. In another embodiment, an advantage is ability of the target cells to differentiate without a requirement for contact inhibition. In another embodiment, the differentiation is a consequence of inhibition of proliferation. Each possibility represents another embodiment of the present invention.

In one embodiment, provided herein are methods for inducing proliferation of a quiescent somatic stem cell. It has been discovered that contacting a stem cell with a material that is less elastic than the elasticity of the naturally occurring in vivo microenvironment of the same type of stem cell is effective to induce proliferation of the stem cell. Embodiments of the present invention thus include contacting the somatic stem cell with a material that comprises compounds that attaches to integrins on the surface of the cell membrane and that has elasticity apparent to the stem cell less than the elasticity of the predominant material in the biological microenvironment of an in vivo somatic stem cell of the same type as the somatic stem cell. For example, the proliferation of quiescent stem cells may be induced by placing them on a glass slide, which has a rigidity of more than 1 gigaPascal (a small fraction of the elasticity of most human or animal tissue types) and which is coated with a material contacting the integrins on the cell. In other embodiments, proliferation of a stem cell may be induced by contacting the cell with a material apparent to the cell having an elasticity of less than 0.1 of the elasticity of the natural in vivo microenvironment of the stem cell. In other embodiments, proliferation may be induced by contacting the stem cell with a material having an elasticity apparent to the stem cell of less than about 0.5 times (e.g., about 0.4 to about 0.5 times) the elasticity of the natural in vivo microenvironment of the stem cell.

In embodiments, the cell may also be provided with nutrient-growth material, for example, including growth factors and serum, for promoting proliferation and sustaining biological activity of the stem cell and its progeny ex vivo. The formulation of the nutrient-growth material for particular cell types is known to those of skill in the art, and no variation in known nutrient-growth materials for particular types of stem cells should be needed to practice this aspect of the present invention.

As with other aspects of the present invention, embodiments of this proliferation-inducing aspect may be practiced with stem cells, including MSCs. The MSCs may be harvested from living tissue, as described in this specification, or derived from other sources such as in vitro cultures and cryogenically frozen stem cells. Such cells may be in a naturally-occurring quiescent state or an artificially-induced quiescent state, and may for example include cells in which quiescence has been induced or maintained using methods of the present invention. Accordingly, cells in which proliferation may be induced according to methods of the present invention may include bone marrow-derived mesenchymal stem cells (MSCs), renal stem cells, hepatic stem cells, skeletal muscle-derived stem cells, bone-derived stem cells, dental pulp MSCs, cardiac muscle-derived MSCs, synovial fluid-derived MSCs, umbilical cord MSCs, and other types of cells that can be identified by one of skill in the art in light of this specification.

The proliferation of stem cells according to the present invention is reversible, enabling alternating states of quiescence and proliferation to be induced into a cell. For example, the methods of the present invention may be used to induce and maintain quiescence in a stem cell, for example by contacting the stem cell with a material comprising compounds that bind to integrins on the cell surface and having elasticity apparent to the cell approximately the same as the elasticity of the in vivo microenvironment of the cell. Then proliferation may be induced in the cell by contacting the cell with a material comprising compounds that attach to integrins and having elasticity apparent to the cell substantially less than the elasticity of the in vivo microenvironment of the cell. Then quiescence may be induced and maintained by contacting the resulting daughter cells with a material including integrin-binding compounds and having elasticity apparent to the cells approximately the same as the in vivo microenvironment of the cells.

In another embodiment, proliferating stem cells are induced into a quiescent state according to a method of the present invention. These quiescent cells may then be induced to proliferate, as described above.

The present invention further provides methods for inducing differentiation of a somatic stem cell in which biological activity is being sustained and quiescence has been induced or is being maintained according to the methods of the present invention. Embodiments of this aspect of the present invention include the step of contacting such cells with a differentiation material comprising chemical stimuli selected to stimulate differentiation of the cells to a predetermined cell type, and providing the cells with a differentiated cell nutrient material for sustaining biological activity of the differentiation-stimulated cells. In some embodiments, the contacting step may be preceded by a step comprising inducing (or permitting) proliferation, for example ex vivo, of the somatic stem cell by contacting the stem cell with a material having elasticity less than the elasticity of the natural microenvironment of the target cell of intended differentiation.

Differentiation may be induced in quiescent or proliferating stem cells sustained in biological activity according to this invention, using methods known or apparent to those of skill in the art in light of this specification. For example, if the stem cell is a human bone marrow-derived mesenchymal stem cell, differentiation of the cell into adipocytes may be effectuated by contacting the cell with an adipogenic medium (as discussed in Example 1) on a substrate with an elasticity of approximately 250 Pa, as described in detail in this specification. Using information that may be obtained from or as described in this specification concerning the rheology of various tissue types as well as the differentiation medium to be used to induce stem cells to differentiate into various types of cells, it would be apparent to those of skill in the art that methods of the present invention may be used to induce a human bone marrow-derived mesenchymal stem cell to differentiate into one or more of at least the following cell types: osteoblasts, chondrocytes, myocytes, adipocytes, beta-pancreatic islet cells, and neuronal cells. More generally, using information on rheology of various tissue types and differentiation media used to induce differentiation of various stem cell types into various types of cells, it would be readily apparent to those of skill in the art to induce differentiation, in any of the stem cell types identified in this specification, into one or more of an osteoblast, a chondrocyte, a myocyte, an adipocyte, a beta-pancreatic islet cell, a neuronal cell, or another cell type.

In embodiments of this aspect of the invention, the differentiated cells are contacted with a medium including nutrients to maintain biological activity of the cells. For example, if a method of the present invention is used to induce a human bone marrow-derived mesenchymal stem cell to differentiate into adipocytes, the resulting adipocytes may be contacted with a nutrient medium in order to sustain their biological activity. The nutrient medium may comprise DMEM (low glucose), fetal bovine serum, and insulin. Other nutrient media, and methods for contacting differentiated cells with them, will be apparent to those of skill in the art in light of this specification.

The present invention further provides an artificial system for inducing or maintaining quiescence and sustainable biological activity of a somatic stem cell. In embodiments, the system includes an extracellular material (ECM) ligand substance for contacting a stem cell, a substrate material linked to the ECM ligand substance, and a medium for providing nutrients to the stem cell and sustaining its biological activity. The ECM ligand substance, when linked to the substrate material, has elasticity similar to the elasticity of the predominant in vivo material in the biological microenvironment of an in vivo stem cell of the same type. Embodiments of the system may be adapted to induce quiescence in any of the cell types in which quiescence may be induced according to the methods of the invention described in this specification. For example, embodiments of the system may be adapted to induce quiescence in a somatic stem cell or an embryonic stem cell, a human stem cell or an animal stem cell, a mesenchymal somatic stem cell (MSC), a bone marrow-derived MSCs, a renal stem cell, a hepatic-derived stem cell, a skeletal muscle-derived MSC, a bone-derived MSC, a dental pulp MSC, a cardiac muscle-derived MSC a synovial-fluid derived MSC or an umbilical cord MSC.

In embodiments, when the ECM ligand substance is linked to the substrate and contacts a stem cell, the ECM material binds to integrins on the surface of the stem cell in a manner that induces the stem cell to enter quiescence, as described in detail in this specification.

In embodiments of such a system of the present invention, there may be a linking material that links the ECM ligand material with the substrate material. For example, when the substrate material comprises a polyacrylamide gel and the ECM comprises a collagen-fibronectin mixture, the linking material may be NHS, including specifically acrylic acid N-hydroxysuccinimide ester. Depending on the nature of the substrate material and the extracellular material, those of skill in the art can readily ascertain linking materials, which may also be characterized as cross-linkers, to be used to link the substrate material and the ECM in various embodiments of systems of the present invention.

In embodiments of the present invention, when the ECM ligand layer is coupled to the substrate, the ECM ligand layer has elasticity apparent to the stem cell substantially similar to the elasticity of the predominant material in the biological microenvironment of an in vivo stem cell of the same type as the stem cell contacting the ECM ligand layer. This apparent elasticity of the ECM ligand layer may be independent of, nearly independent of, or dependent on the elasticity of the substrate. In embodiments, the elasticity of the substrate is substantially similar to the elasticity of the predominant material in the biological microenvironment of an in vivo stem cell of the same type as the stem cell contacting the ECM ligand layer, and the ECM ligand layer presents to the stem cell substantially the same elasticity as the elasticity of the substrate to which it is coupled.

The artificial system of the present invention may be implemented using a variety of structures. In embodiments, the substrate material forms a matrix, and the ECM is dispersed in the matrix. In embodiments, a linking material may also be dispersed in the substrate matrix for linking the material of the substrate matrix with the ECM. For example, according to one embodiment, a 5:1 mixture of collagen derived from rat tails (0.5 mg/ml) and fibronectin derived from humans (0.1 mg/ml), and an acrylic acid N-hydroxysuccinimide ester (NHS) cross-linker, are dispersed in a polyacrylamide gel. The gel is formulated so that the elasticity of the structure is about 250 Pa. When bone marrow-derived MSCs are contacted with the polyacrylamide-NHS-fibronectin-collagen structure, they are induced to enter quiescence. When the MSCs contacting the structure are also provided with suitable nutrient material, their biological activity in a quiescent state is maintained.

In embodiments, the substrate material forms a layer, and the ECM forms a layer linked, directly or indirectly, with the substrate layer. In other embodiments, the linking material forms a linking layer that links the ECM ligand layer with the substrate layer. The linking layer may serve to present the elasticity of the substrate to the ECM ligand layer in a manner that enables the ECM ligand layer to present that elasticity to the stem cell in which quiescence is to be induced. In an embodiment, the linking layer includes appropriate cross-linking compositions and other materials that serve these functions. For example, the coupling layer may comprise NHS or, in specific embodiments, acrylic acid N-hydroxysuccinimide ester.

In embodiments, the substrate material is a polyacrylamide gel. As is known in the art, the elasticity of polyacrylamide gels may be adjusted by changing the concentrations of acrylamide and bisacrylamide in the gel. It would be apparent to those of skill in the art, in light of this specification, how to make polyacrylamide or other gels or substrate materials for use in the systems of the present invention.

As is further apparent in light of this specification, embodiments may utilize other structures. For example, a quasi 3-D structure may be created by seeding stem cells on an ECM layer as described above, settling the cells onto the ECM layer by submerging the system with cells in medium, and placing on the cells another ECM layer with appropriate apparent elasticity, as described further in Example 1.

In another embodiment, an advantage of methods and compositions of the present invention is resistance of the matrix or gel to proteolytic degradation. In another embodiment, an advantage is resistance to active remodeling by the cells. In another embodiment, an advantage is resistance of heterothermic (e.g. salmon) fibrin to proteases secreted by mammalian neurons compared to mammalian (e.g. human or bovine) fibrin. In another embodiment, an advantage is lower incidence of infectious disease transfer of heterothermic (e.g. salmon) fibrin compared to mammalian (e.g. human or bovine) fibrin. Each possibility represents another embodiment of the present invention.

In another embodiment, the target cell of methods and compositions of the present invention is an immortalized MSC.

In another embodiment, provided herein is a method of inducing growth arrest of an immortalized MSC, comprising the step of culturing the immortalized MSC in a gel or matrix of the present invention, thereby inducing growth arrest of an immortalized MSC. In another embodiment, provided herein is a method of inhibiting growth of an immortalized MSC population, comprising the step of culturing the immortalized MSC in a gel or matrix of the present invention, thereby inhibiting growth of an immortalized MSC population. Each possibility represents a separate embodiment of the present invention.

In another embodiment, the target cell of methods and compositions of the present invention is a transformed cell. In another embodiment, the transformed cell is a melanoma cell. In another embodiment, the transformed cell is any other type of transformed cell known in the art. Each possibility represents a separate embodiment of the present invention.

As provided herein, M2 cells exhibited a larger size and larger cell population on stiffer substrates. In another embodiment, an increased cell population is a result of increased growth of the cells on stiff substrates. In another embodiment, an increased population is due to increased death of cells on soft substrates. Each possibility represents a separate embodiment of the present invention.

In another embodiment, provided herein is a method of inducing growth arrest of a transformed cell, comprising the step of culturing the transformed cell in a gel or matrix of the present invention, thereby inducing growth arrest of a transformed cell. In another embodiment, provided herein is a method of inhibiting growth of a transformed cell population, comprising the step of culturing the transformed cell in a gel or matrix of the present invention, thereby inhibiting growth of a transformed cell population. Each possibility represents a separate embodiment of the present invention.

In another embodiment, a soft substrate of methods and compositions of the present invention results in an increase in inactive GDP-bound form of a GTP protein in the target cells. In another embodiment, the GTP protein is Rho. In another embodiment, the GTP protein is Rac. In another embodiment, the GTP protein is Cdc42. In another embodiment, the GTP protein is any other GTP protein known in the art. Each possibility represents a separate embodiment of the present invention.

In another embodiment, the Rho family member signals via formation of focal adhesions. In another embodiment, activation of Rho inhibits expression of $p21^{WAF1/clp1}$. In another embodiment, inhibition of p21 activates cyclin-dependent kinases (CDKs). In another embodiment, activation of Rho induces downregulation and degradation of $p27^{Klp1}$, another CDK inhibitor. In another embodiment, activation of Rho induces ROCK, resulting in activation of the Ras-Raf-MEK-ERK pathway. In another embodiment, this pathway induces Ras-mediated cyclin-D1 transcription. In another embodiment, this induces G1-phase progression. Together, Rho activation was shown to lead to G1-phase progression. In another embodiment, activation of Rac or Cdc42 upregulates cyclin-E1 and cyclin-D1, resulting in G1-phase progression. In another embodiment, activation of a Rho-family small GTP-binding protein results in signal transduction to enhance cell cycle progression. Each possibility represents a separate embodiment of the present invention.

In another embodiment, a soft substrate of methods and compositions of the present invention decreases the contractility of the actomyosin system of the target cell. In another embodiment, this induces target cells to cease proliferation. In another embodiment, this induces target cells to become competent for further stimuli to re-initiate proliferation. In another embodiment, this induces target cells to become competent for further stimuli to commit to terminal differentiation. Each possibility represents a separate embodiment of the present invention.

In another embodiment, a soft substrate of methods and compositions of the present invention induces activation of actomyosin. In another embodiment, the soft substrate induces actomyosin regulated by Rho. In another embodiment, the soft substrate induces myosin II. In another embodiment, the soft substrate induces myosin II regulated by Rho. Each possibility represents a separate embodiment of the present invention.

In another embodiment, a composition of methods and compositions of the present invention further comprises an activator of a Rho family member. In another embodiment, the composition further comprises an inhibitor of a Rho family member. In another embodiment, the Rho family member is Rho. In another embodiment, the Rho family member is Rac. In another embodiment, the Rho family member is Cdc42. In another embodiment, the Rho family member is any other Rho family member known in the art. Each possibility represents a separate embodiment of the present invention. In another embodiment, the composition further comprises an activator of actomyosin. In another embodiment, the composition further comprises an inhibitor of actomyosin. In another embodiment, the composition further comprises an activator of myosin II. In another embodiment, the composition further comprises an inhibitor of myosin II. Each possibility represents a separate embodiment of the present invention.

Methods for polymerizing acrylamide gels are well known in the art. In another embodiment, 1.5 µl TEMED (FisherBiotech CAS no. 110189) and 5 µl 10% ammonium persulfate are added with the appropriate amount of $H_2O$ to yield a final volume of 1,000 µl, the solution is pipetted onto a cover slip, and a top cover slip is placed on top of the solution, then peeled away 10 minutes later. Each method represents a separate embodiment of the present invention.

In another embodiment, to crosslink adhesion proteins onto the gel or matrix, a heterobifunctional crosslinker is utilized. In another embodiment, the heterobifunctional crosslinker is sulfo-SANPAH (sulfosuccinimidyl6(4'-azido-2'-nitrophenyl-amino)hexanoate, Pierce no. 22589). In another embodiment, the heterobifunctional crosslinker is any other heterobifunctional crosslinker known in the art. In another embodiment, sulfo-SANPAH is used as follows. 1 mg/ml sulfo-SANPAH is dissolved in $H_2O$, and 200 µl of this solution is pipetted onto the gel surface. The polyacrylamide gel is then placed 6 inches under an ultraviolet lamp and irradiated for 10 min. It is then washed three times each with 3 mL of 200 mM HEPES, pH 8.6. After the last HEPES solution is aspirated, 200 µl of a 0.14 mg/ml fish fibronectin solution (Sea Run Holdings, South Freeport, Me.) or 0.14 mg/ml type I collagen is pipetted on top of the polyacrylamide gel. The multiwell plate housing the gels is then incubated at 5° C. for 4 h. Each method represents a separate embodiment of the present invention.

In another aspect of the present invention, a kit of components may be provided for assembling a system as described above or for otherwise carrying out the methods of the present invention. In an embodiment, such a kit includes as separate components: (1) a substrate, or materials for making a substrate; (2) optionally materials for making and/or applying a coupling layer; and (3) materials for making and/or applying ECM ligand material to form an ECM ligand layer. The substrate component may, for example, comprise a polyacrylamide gel of a predetermined elasticity, a polyacrylamide gel with materials for adjusting the elasticity of the gel to a predetermined elasticity or range of elasticities, or materials for making a gel or other suitable substrate with the desired elasticity. In embodiments, the kit includes a device for mounting or holding the gel in order to facilitate the application of the ECM ligand layer and optionally a coupling layer for coupling the substrate to the ECM ligand layer. As is apparent to those of skill in the art in light of this specification, various components of the kits of this invention may be combined in order to facilitate storage, shipment and assembly of the kits.

Embodiments of such a kit also may include materials for making and/or applying the ECM ligand layer. For example, the kit may include ECM ligand material for direct application to the substrate. In other embodiments, the kit may include individual components or ingredients of the material of the ECM ligand layer, with instructions for making and applying it to the other components of the kit. Optionally, the kit may include materials and instructions for assembling and applying a coupling layer for coupling the substrate to the ECM ligand layer. In a specific embodiment, a kit of a system of the present invention for inducing quiescence in a human bone marrow-derived MSC includes the following:

(a) a glass Petri dish (or other apparatus for supporting the substrate and holding the rest of the components);

(b) materials for making a polyacrylamide gel with about 250 Pa hardness to serve as the substrate, including appropriate amounts of acrylamide and bisacrylamide;

(c) acrylic acid N-hydroxysuccinimide ester (NHS) crosslinker for applying to the gel in order to form a coupling layer; and (d) materials for making an ECM ligand layer, including the materials identified in Example 1, for making a 1:5 fibronectin-collagen extracellular material.

In an embodiment, a kit of the present invention comprises a polyacrylamide gel formulated with an elasticity for inducing quiescence in stem cells of a specified type; a solution including cross-linking compositions for application to the gel; extracellular material formulated to bind to integrins on the surface of the specified type of cells; and, optionally, suitable nutrient material (which may also be prepared by users) for the cells to be induced into quiescence.

In some embodiments of the kit, the kit comprises one layer of material that provides both elasticity and ECM ligands. In another embodiment, the kit may comprise the following three layers of materials:

a) a gel substrate that confers elasticity to the system;
b) ECM ligands; and
c) crosslinkers that connect ECM ligands to the substrate.

In embodiments of kits of the present invention, the components of the kit are placed in a receptacle such as a bag or plastic package containing phosphate-buffered saline (PBS). In some embodiments, the receptacle may also contain preservatives such as sodium azide. The components may be hydrated in the kit, for example, during storage. In some embodiments, the receptacle is sealed and/or protected with appropriate scaffolds to avoid damage to the system. The kit may be shipped at low temperature, such as about 2° C. to about 8° C.

In embodiments of kits of the present invention, users can open the receptacle and place the components of the kit onto an appropriate material, such as a tissue culture plate. Users can also remove any hard material on top of the components to expose the ECM ligands and wash the components with a buffer such as PBS. Users can then seed cells onto the system by putting a cell suspension that comprises cells, medium, and serum, as necessary.

The systems and methods of the present invention may be practiced in vivo as well as ex vivo. Such systems may, for example, include porous structures for insertion in specific tissues or the circulatory system for maintaining a stem cell in quiescence within the body. For example, stem cells, corresponding ECM and, optionally, linking material, may be dispersed in a polymeric matrix that has appropriate elasticity apparent to the stem cells to induce or maintain quiescence, and that also has sufficient porosity to permit in vivo nutrients to reach the cell and to permit proteins and other factors expressed by the cell to leave the matrix. Other embodiments may include cassettes or other devices that induce or maintain quiescence in stem cells, and that may be implanted into a host.

A further aspect of the present invention encompasses a quiescent stem cell sustained in biological activity ex vivo. Examples of such a stem cell include a somatic stem cell or an embryonic stem cell, a human stem cell or an animal stem cell, a mesenchymal stem cell (MSC), a bone marrow-derived MSCs, a renal stem cell, a hepatic-derived stem cell, a skeletal muscle-derived MSC, a bone-derived MSC, a dental pulp MSC, a cardiac muscle-derived MSC a synovial-fluid derived MSC or an umbilical cord MSC. In embodiments, the systems or methods of the present invention are used to induce or maintain a stem cell in a quiescent state, and to sustain the biological activity of such quiescent stem cells.

Accordingly, in one embodiment, provided herein is an apparatus for modulating growth of a mesenchymal stem cell comprising: a gel matrix having a rigidity in a range of 150-750 Pa; and an adipocyte induction medium, wherein said gel or matrix is coated with a type 1 collagen, a fibronectin, or a combination thereof.

In other embodiments, the gels and matrices of any of the methods described above have any of the characteristics of a gel or matrix of compositions of the present invention. Each characteristic represents a separate embodiment of the present invention.

EXPERIMENTAL DETAILS SECTION

Example 1

Measurement of the Rigidity of Various Tissues and Preparation of Polyacrylamide Gels Approximating the Rigidities of the Tissues Materials and Experimental Methods Preparation of Polyacrylamide Gels Acrylamide and bisacrylamide (Fisher Biotech, Loughborough, Leicestershire, UK) solutions were prepared to contain a constant polymer mass of 7.5% and bisacrylamide concentrations of 0.01%, 0.03% or 0.3% to alter stiffness. Acrylamide, bisacrylamide, ammonium persulfate, and N,N,N',N'-tetramethylethylenediamine (TEMED) under a non-aqueous layer of toluene containing 0.5% acrylic acid N-hydroxy succinimide ester (Sigma, St. Louis, Miss.) was polymerized between two coverslips, chemically modified as follows: 200 µl of 0.1 N NaOH was pipetted to cover the surface of a 25-mm-diameter glass cover slip (Fisherbrand, catalog no. 12-545-102; Fisher Scientific, Pittsburgh, Pa.) for 5 min. The NaOH solution was aspirated, and 200 µl of 3-APTMS (3-Aminopropyltrimethoxysilane, Sigma no. 28-1778, Sigma, St. Louis, Mo.) was applied for 3 min. The glass cover slip was thoroughly rinsed with de-ionized water to wash away any remaining 3-APTMS solution, and 200 µl of 0.5% v glutaraldehyde (Sigma no. G7651) in $H_2O$ was added onto the cover slip for 20 min. The glass cover slip was rinsed with water, an 18-mm-diameter glass cover slip was placed on top of a piece of parafilm inside a tissue culture dish, and a few drops of a 10% by volume Surfasil solution (Pierce no. 42800, Pierce, Rockford, Ill.) in chloroform was pipetted onto the parafilm near the cover slip. The tissue culture dish with a half-closed lid was placed inside a vacuum desiccator for 10 min.

The N-succinimidyl acrylate incorporated at the surface of the gel was reacted with 0.2 mg/ml laminin (Collaborative Biomedical, Bedford, Mass.) to produce a uniform coating of adhesive ligands. After washing with HEPES buffer to remove traces of un-polymerized solvent, wells containing the polyacrylamide (PA) gels were filled with culture medium and allowed to equilibrate overnight at 37° C.

Viscoelastic Characterization of Material Scaffolds

The dynamic shear moduli of gels were measured on a strain-controlled rheometrics fluids spectrometer III (Rheometrics, Piscataway, N.J.). A 500-µL sample was polymerized between two steel plates, and the shear modulus $G'(\omega)$, which describes elastic resistance, was calculated from the shear stress in phase with a 2% oscillatory (1 rad/s) shear strain. The dynamic shear moduli of tissues were similarly measured. An 8-mm diameter sample was cut using a stainless steel punch and placed between the plates. Short-term $G'(\omega)$ was measured by oscillation at 2% strain and the long-term shear modulus $G(t)$ was measured by applying a 10% steady strain and allowing the sample to relax for 30 s.

Results

Polyacrylamide gels were prepared and coated with a mixture of 0.14 mg/ml type I collagen and 0.14 mg/ml fish fibronectin. By adjusting the concentration of acrylamide and bisacrylamide, a wide range of rigidity was achieved (FIG. 1A). The rigidity of polyacrylamide gels does not affect the amount and the distribution of the extracellular matrix on gels. In vitro rheometery was also used to determine the elastic properties of tissues relevant to mesenchymal stem cells (Table 1). Polyacrylamide gels with G' of 200 Pa (herein used as one example of "soft gels" and referred to as such) or 7500 Pa (herein used as one example of "stiff gels" and referred to as such) were prepared; the soft gels mimic the rigidity of bone marrow and fat tissues.

TABLE 1

Rigidity of tissues.

| Tissue | Rigidity (Pa) |
| --- | --- |
| bovine bone marrow | 225 ± 25 |
| rat subcutaneous fat | 157 ± 36 |
| rat visceral fat | 130 ± 40 |

TABLE 1-continued

Rigidity of tissues.

| Tissue | Rigidity (Pa) |
|---|---|
| rat liver | 403 ± 28 |
| rat skeletal muscle | 2251 ± 166 |

Rat tissues were obtained from three Sprague-Dawley rats.

Thus, polyacrylamide gels were prepared that mimic the rigidity of biological tissue.

Example 2

Cell Shape and F-Actin Structure of hMSC on Soft and Stiff Gels

Materials and Experimental Methods hMSC were sparsely seeded on either stiff gels or soft gels coated with collagen type 1 and fibronectin. Cells were incubated for 24 hours in DMEM+10% fetal calf serum, fixed, and stained with Alexa Fluor 488 phalloidin.

Results

Figure 1B:
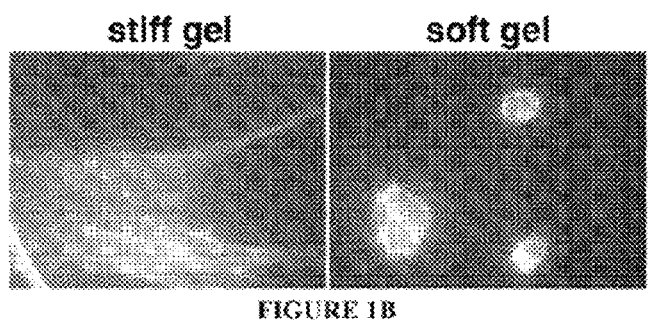
Figure 1C:
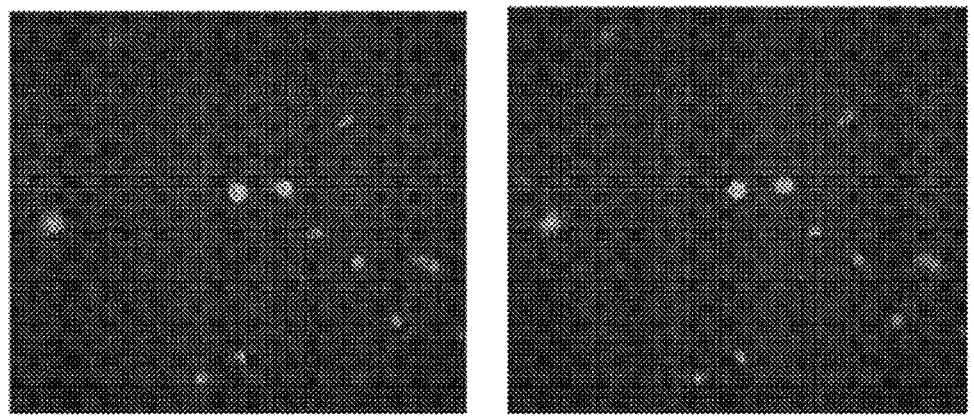

The effect of extracellular matrix rigidity on the shape and F-actin structure of hMSC (human mesenchymal stem cells) was investigated. Cells were incubated in the presence of serum on matrices with various rigidities for 24 hours to allow adherence and spreading. hMSC seeded on stiff gels or glass adopted a spindle shape and exhibited stress fibers and cortical F-actin (as shown by Alexa Fluor 488 phalloidin staining), whereas cells seeded on soft gels exhibited a rounded appearance, lacked stress fibers, and contained F-actin aggregates (FIG. 1B-C).

Thus, hMSC sense the rigidity of the extracellular matrix, which influences their shape and F-actin structure.

Example 3

Inhibition of hMSC Proliferation on Soft Gels

Figure 2:
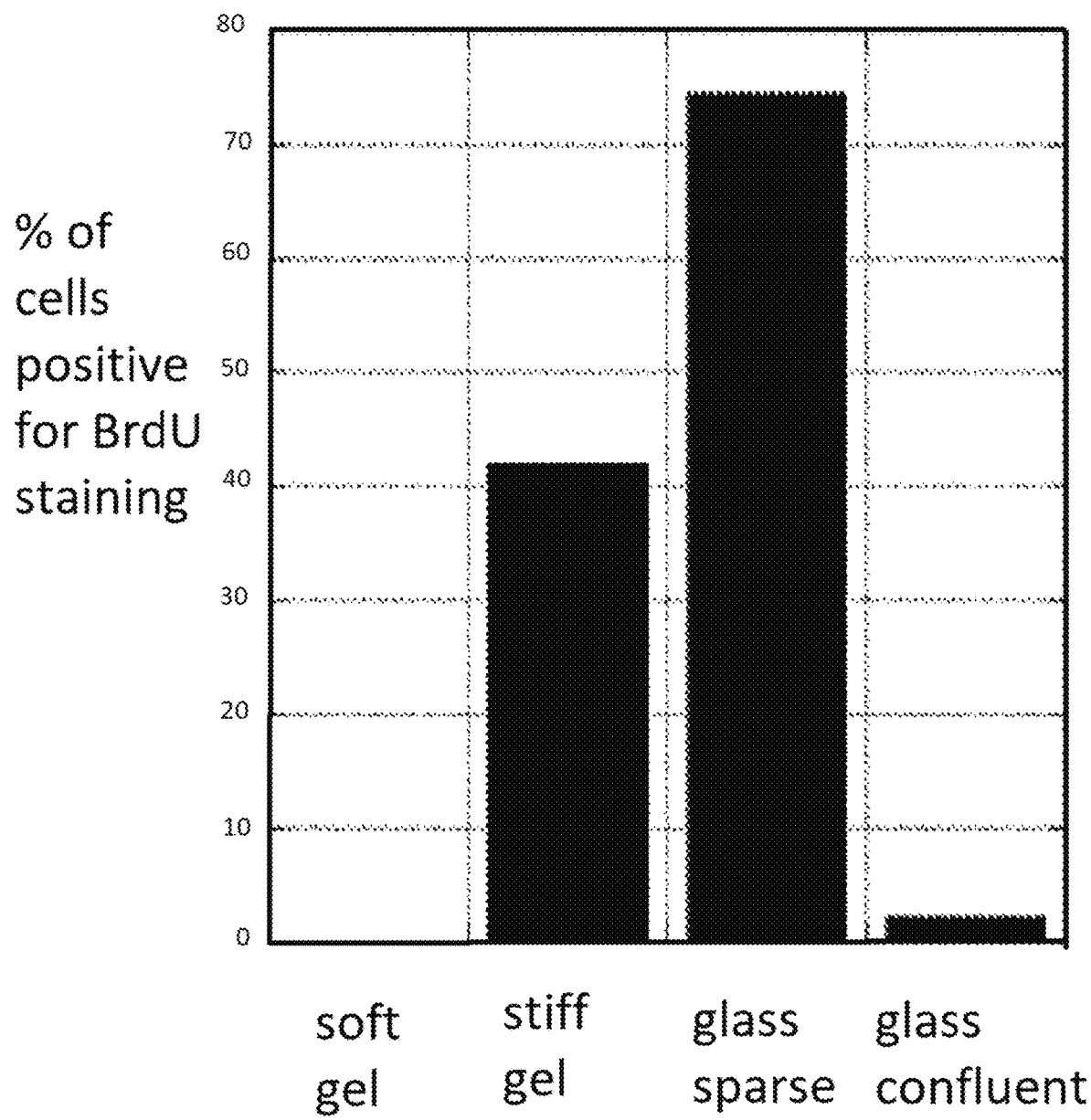
FIG. 2. BrdU incorporation into hMSC.

Materials and Experimental Methods hMSC were incubated with BrdU (Invitrogen, Carlsbad, Calif.) overnight in the presence of serum. Cells were fixed and immunostained for BrdU (Invitrogen). More than 50 cells were counted for three times in randomly chosen fields Results 5-bromo-2'-deoxyuridine 5'-triphosphate (BrdU) incorporation was measured in hMSC as a marker of cell cycle progression (FIG. 2). Cells were seeded sparsely on soft gels, stiff gels or glass surfaces, all of which were coated with collagen type 1 and fibronectin. As a control, confluent cells on glass surface were also prepared. As expected, hMSC sparsely seeded on glass surfaces efficiently incorporated BrdU, indicating a high level of proliferation. When cells were confluent on glass surface, very few hMSC incorporated BrdU due to a contact inhibition. 42% of hMSC on stiff gels incorporated BrdU, indicating a large population of cells was proliferating, although significantly less than that of sparsely seeded cells on a glass surface. On the other hand, no hMSC on soft gels incorporated BrdU, even though the cells were viable as assessed by lack of Trypan Blue staining. Further, continued incubation of sparsely seeded hMSC on matrices yielded a different cell density depending on the rigidity of matrices with higher density on stiffer matrices.

Thus, soft matrices inhibit proliferation of hMSC even in the presence of serum.

Example 4 hMSC on Soft Gels are Competent to Differentiate into Adipocytes

Materials and Experimental Methods

Adipocyte Differentiation Studies hMSC from cell suspensions were seeded onto collagen type 1 plus fibronectin-coated 96-well tissue culture plates at a density of $3.5 \times 10^4$ cells/well. After incubating cells in DMEM containing 10% FCS (growth medium, "GM") for 24 hours, cells were induced to differentiate into adipocytes by incubating 3 for days (2 cell cycles) in Adipogenic Induction Medium (AIM) (GM, 1 µM dexamethasone, 200 µM indomethacin, 10 µg/ml insulin, and 0.5 mM methyl-isobutylxanthine) then maintaining in Adipogenic Maintenance Medium (GM, 10 (µg/ml insulin). 8 days after switching to AIM, adipocyte differentiation was evaluated either by Oil Red O staining (Sigma-Aldrich, St. Louis, Mo.) or by immuno-staining for PPARγ2 using anti-PPARγ2 antibodies. More than 50 cells were counted for three times in randomly chosen fields. Anti-PPARγ2 antibodies were provided by Dr. Mitchell A. Lazar, University of Pennsylvania.

Results

Figure 3A:
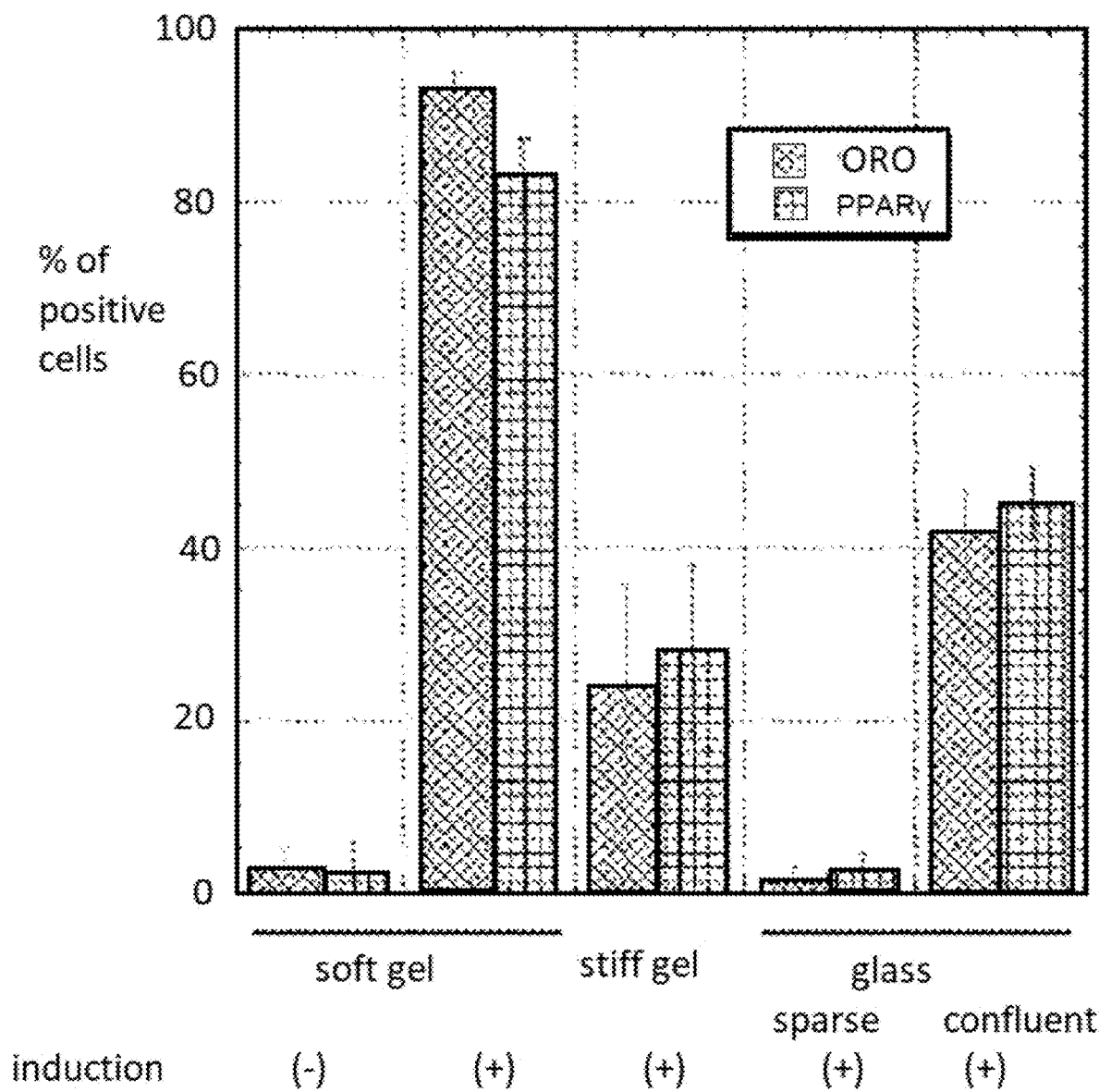

To confirm the viability of hMSC on soft gels, their ability to differentiate into adipocytes was measured in two ways; (a) immunostaining of peroxisome proliferators-activated receptors gamma 2 (PPARγ2), one of key transcription factors for adipogenesis, and (b) Oil Red O-staining to measure lipid accumulation. When confluent hMSC on a glass surface were induced for adipocyte differentiation by a mixture of dexamethasone, indomethacin, 3-isobutyl-1-methyl-xanthine and insulin in fetal calf serum-containing medium, approximately 40% of cells exhibited an adipocyte phenotype (FIG. 3A). By contrast, on soft gels with induction, the differentiation rate reached more than 80%, significantly higher than on glass; without induction, no adipocyte differentiation was observed. Further, hMSC sparsely seeded on glass exhibited a high level of proliferation (FIG. 2) and did not differentiate into adipocytes (FIG. 3B). These results further indicate that hMSC might need to leave the cell cycle as a prerequisite for terminal differentiation.

Thus, hMSC sparsely seeded on soft gels are fully viable and are competent for adipocyte differentiation.

Example 5

F-Actin Structure in Astrocytes Seeded on Either Stiff or Soft Gels

To further characterize and quantify the response of cells to matrix rigidity, the effect of extracellular matrix stiffness on F-actin structure was also tested in astrocytes. Primary astrocytes were isolated from Sprague-Dawley rat embryos as follows: Embryos (E17-E19) were removed by caesarean section from a timed-pregnant Sprague-Dawley rat and the cortices were removed. Tissue was digested in trypsin/

DNase at 37° C., centrifuged (1000 g×5 min), and filtered to derive a cell suspension. For cultures containing both neurons and glial cells, cells were plated directly onto substrates. Primary astrocyte cultures were maintained for 14 days in culture with a series of trypsinizations to remove neurons. Cultures used for experiments were >98% astrocytes as determined by GFAP immunocytochemistry. Cells were grown in an incubator at 37° C. and 5% $CO_2$ in Dulbecco's modified Eagle's medium (BioWhittaker, East Rutherford, N.J.) supplemented with Ham's F12 (Sigma) and 5% fetal bovine serum (Hyclone, Logan, Utah) for 7 days followed by an additional 5 days culture in Neurobasal (Gibco, Carlsbad, Calif.) also supplemented with 5% fetal bovine serum, 2 mM 1-glutamine, 50 mcg/mL streptomycin, and 50 units/mL penicillin.

Figure 4:
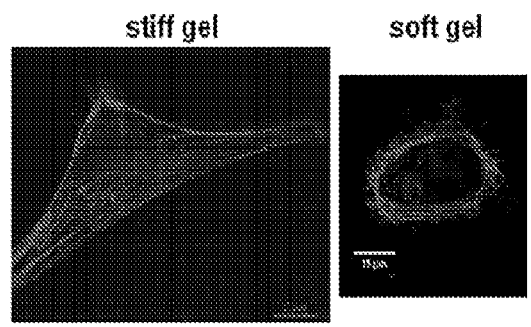
FIG. 4. F-actin structure in astrocytes seeded either on stiff or soft gels.

Cells were incubated in the presence of serum on either stiff (11 kPa) or soft (150 Pa) polyacrylamide gels for 48 hours to allow adherence and spreading. Cells were fixed, and F-actin structure was visualized with phalloidin. As shown in FIG. 4, stress fibers and cortical F-actin were observed in astrocytes plated on stiff gels. By contrast, in astrocytes plated on soft gels, stress fibers were not present and only cortical actin shells were observed. Thus, astrocytes on soft gels sensed the flexibility of the matrix and consequently did not exhibit stress fibers.

Example 6

Low Level of Rho GTP-Loading in Astrocytes on Soft Gels

Materials and Experimental Methods

Rhotekin Pulldown Assay

Cells were washed with ice-cold Tris-buffered saline and lysed in RIPA buffer (50 mM Tris, pH 7.2, 1% Triton X-100, 0.5% sodium deoxycholate, 0.1% SDS, 500 mM NaCl, 10 mM $MgCl_2$, 10 μg/ml each of leupeptin and aprotinin, and 1 mM PMSF). Cell lysates were clarified by centrifugation at 13 000×g at 4° C. for 10 min, and equal volumes of lysates were incubated with GST-RBD (20 μg) beads at 4° C. for 45 min. Beads were washed 4 times with buffer B (Tris buffer containing 1% Triton X-100, 150 mM NaCl, 10 mM $MgCl_2$, 10 μg/ml each of leupeptin and aprotinin, and 0.1 mM PMSF). Bound Rho proteins were detected by Western blotting using a monoclonal antibody against RhoA (Santa Cruz Biotechnology). Densitometry analysis was performed using AlphaImager™ system (Alpha Innotech). The amount of RBD-bound Rho was normalized to the total amount of Rho in cell lysates for the comparison of Rho activity (level of GTPbound Rho) in different samples.

Results

Figure 5:
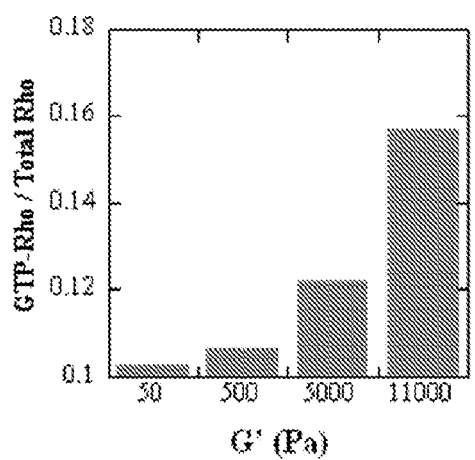
FIG. 5. Quantification of increase in Rho activity from soft to hard gels. Astrocytes were seeded on polyacrylamide gels with various stiffness. GTP-loading level of Rho was quantified.

To determine whether or not soft gel-induced loss of stress fibers in astrocytes is associated with inactivation of Rho, astrocytes were seeded on polyacrylamide gels with various rigidities and incubated in the presence of serum for 48 hours. Cell lysates were prepared, and GTP-loading of Rho was assayed using purified GST-Rhotekin and a Rhotekin pulldown assay. The ratio of GTP-bound vs. total Rho was calculated. Astrocytes on soft gels exhibited a low level of GTP-bound Rho (FIG. 5), indicating attenuation of Rho activity in astrocytes on a soft matrix, results in absence of stress fibers in the cells.

Example 7

Melanoma Cells Modulate their Spreading, Based on the Rigidity in the Extracellular Matrix Materials and Experimental Methods M2 cells were sparsely seeded on matrices of various rigidities coated with a mixture of collagen type 1 and fibronectin. After 24 hours of incubation, cell area was measured by tracing cell boundaries. More than 30 cells were counted for 3 times in randomly chosen fields.

Results

Figure 6:
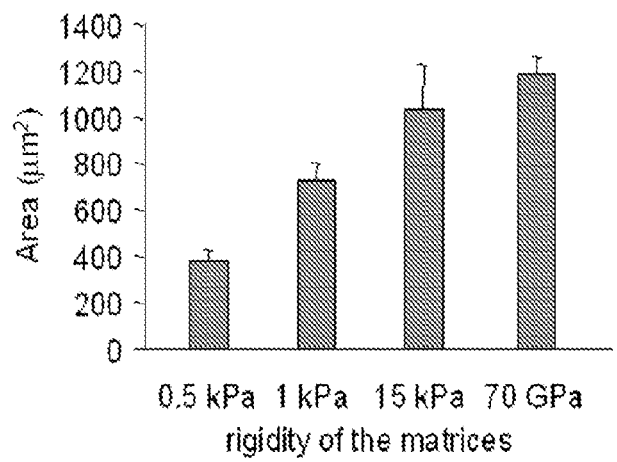
FIG. 6. Melanoma cells spread more on stiff matrices. Graphical representation of area.

To test whether transformed cells modulate their behavior according to the level of rigidity in the extracellular matrix, the effect of rigidity on cell spreading was measured in human melanoma cell lines, termed M2 cells. As shown in FIG. 6, M2 cells exhibited a larger size on stiffer substrates. Thus, transformed M2 cells have an ability to modulate their behavior (for example, cell spreading) according to the mechanical properties of the matrix.

Example 8

Reduced Amount of Melanoma Cells on Soft Gels

Figure 7:
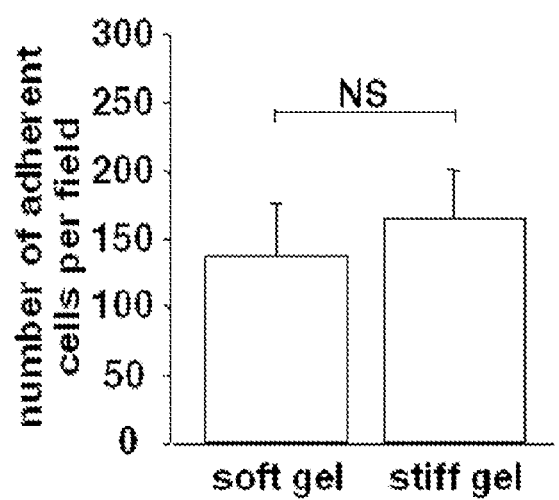
FIG. 7. Melanoma cells adhered to soft and stiff gels with same efficiency.
Figure 8:
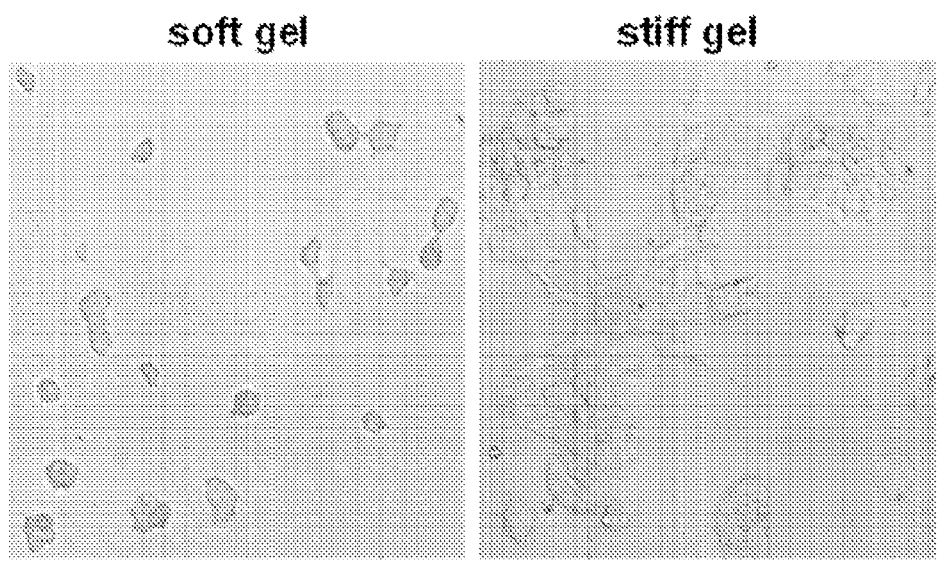
FIG. 8. Larger population of melanoma cells on stiff gels.
Figures 9A, 9B, 9C, 9D, 9E, 9F, 9G, 9H, 9I:
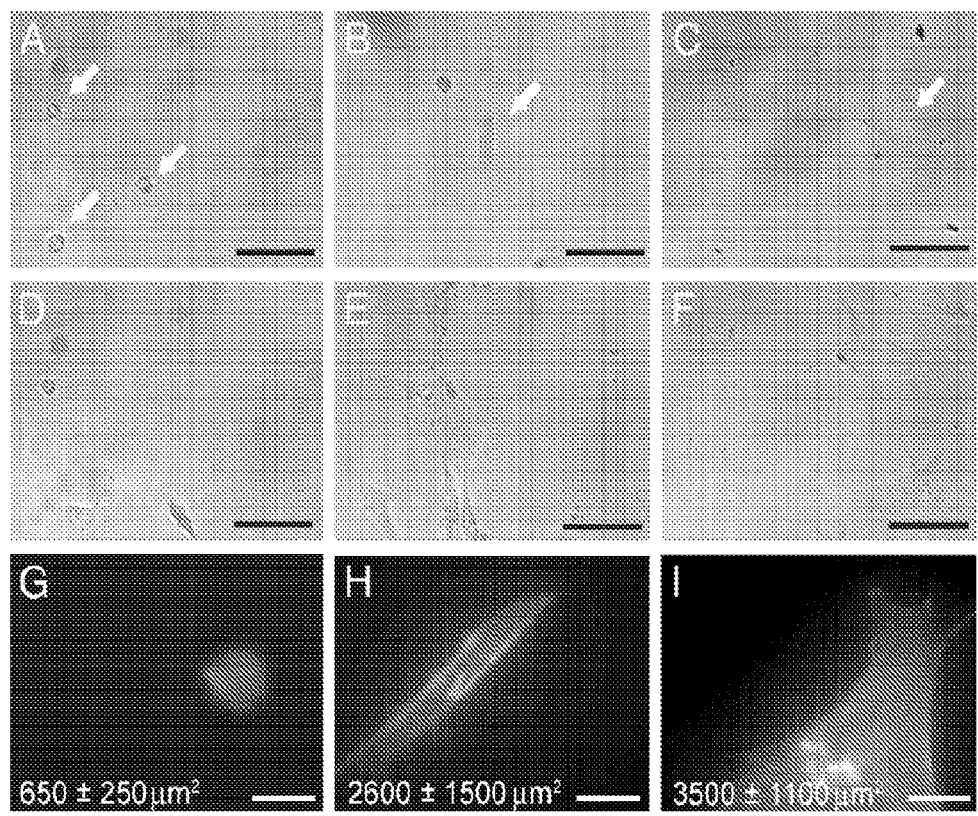
FIG. 9 show images of human MSCs on several substrates of different elasticities according to various embodiments of the present invention.
Figure 10:
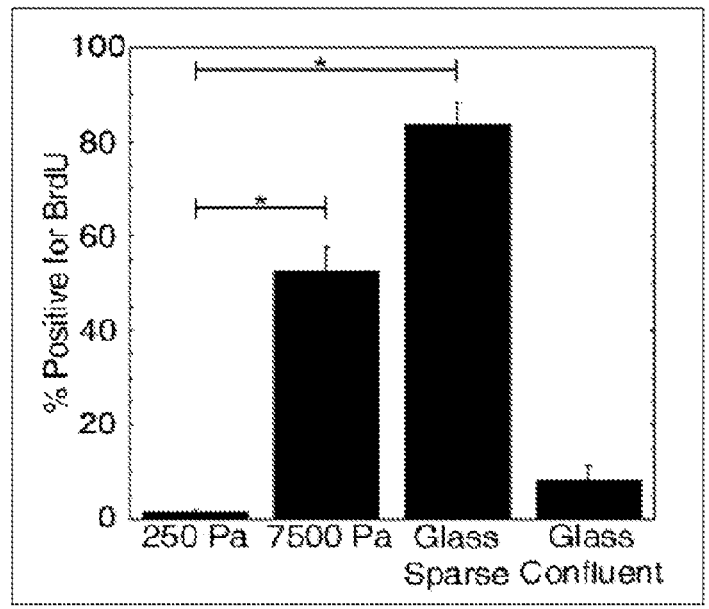
FIG. 10 shows the amount of bromodeoxyuridine (BrdU) uptake into human MSCs on substrates of varying elasticities according to various embodiments of the invention.
Figures 11A, 11B, 11C, 11D:
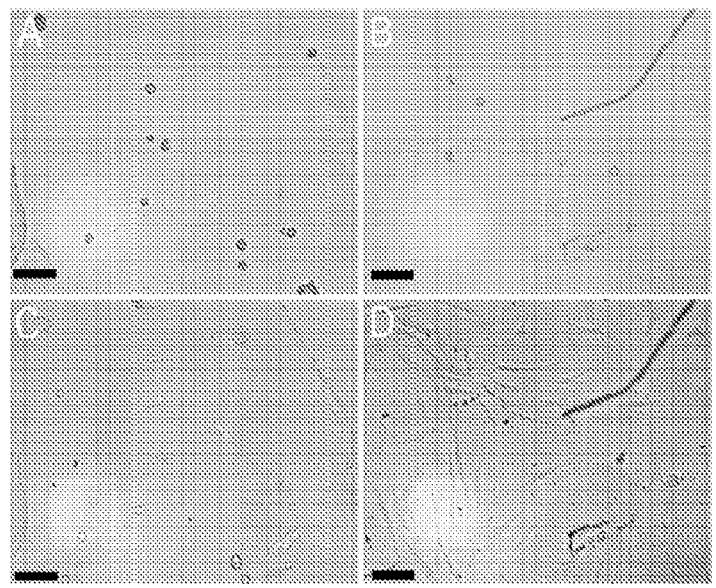
FIG. 11 shows (A-D) an illustration of the effect of a quasi 3D environment on stem cell shape and proliferation according to various embodiments of the invention.
Figure 12:
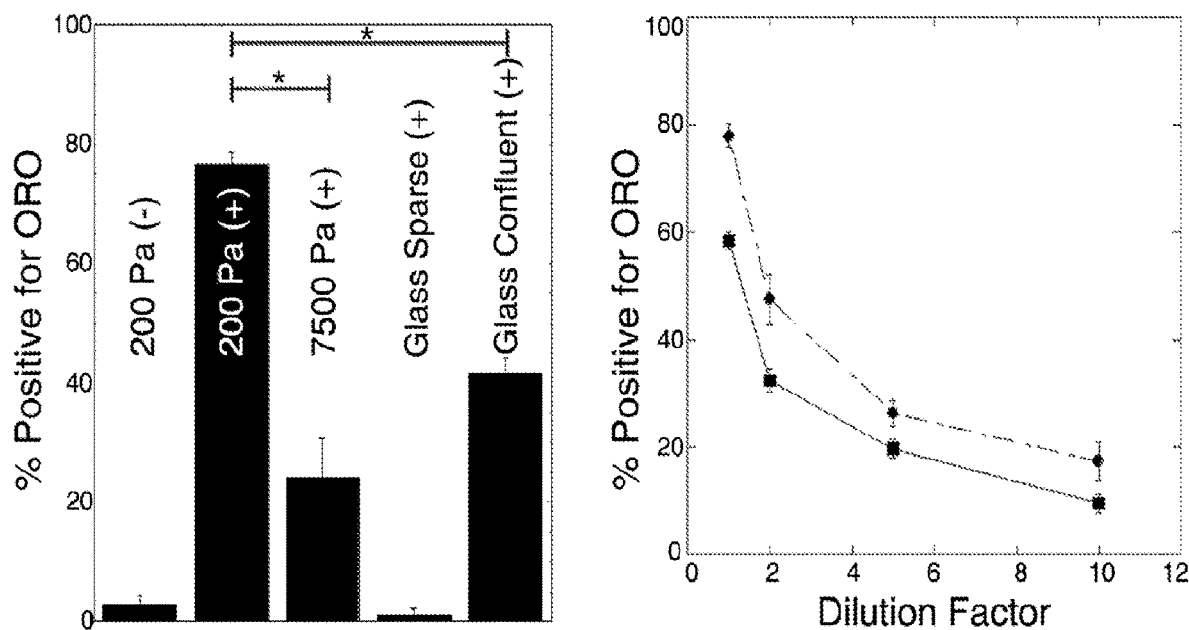
FIG. 12 shows the response of human MSCs to adipogenic induction media according to various embodiments of the invention.
Figure 13:
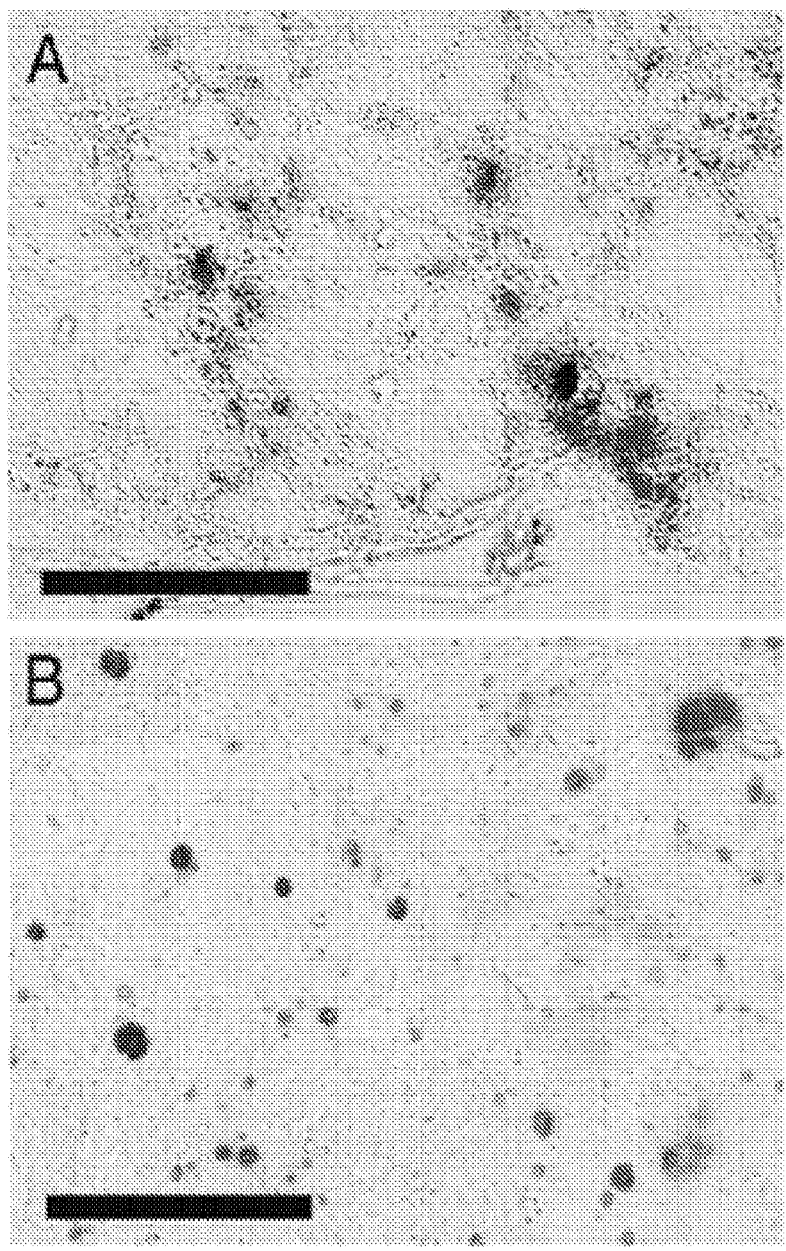
FIG. 13 shows calcium deposition visualized with Alizarin Red S after stimulation of human MSCs with osteoinduction media according to various embodiments of the invention.

To determine the effect of matrix rigidity on the size of M2 cell population, M2 cells were seeded onto soft or stiff gels (the same number on each) and coated with a mixture of type I collagen and fibronectin. Efficiency of cell adherence to each substrate was evaluated after 24 hours of incubation in the presence of serum, when M2 cells were fully adhered and spread on both gels. As shown in FIG. 7, there was no significant difference in the number of adhered cells between soft and stiff gels, indicating the matrix rigidity does not affect adherence of M2 cells. After a 72-hour incubation, although the same number of cells adhered to each substrate (FIG. 7), the additional 48 hours of incubation caused a significantly larger cell population on stiff gels (FIG. 8). No noticeable difference in the number of cells floating in the medium was observed between soft and stiff gels after 72 hours of incubation.

These results further demonstrate methods of quantify responses of hMSC to soft substrates.

Example 9

Use of Soft Gels for Long-Term Preservation of hMSC Without Attenuating Viability and Self-Renewal Materials and Experimental Methods Soft polyacrylamide gels with G' of approximately 200 Pa coated with a mixture of type I collagen and fibronectin are prepared on glass coverslips as described for Example 1. Polyacrylamide gels are placed in 6-well plates covered with 1% agarose gel, to avoid cell adhesion outside of polyacrylamide gels, or glass coverslips. $5 \times 10^4$ passage 2 hMSC are seeded either onto soft polyacrylamide gels or directly onto 6-well tissue culture plates coated with type 1 collagen plus fibronectin, and are incubated in DMEM supplemented with 10% fetal calf serum (FCS). Identical hMSC samples are suspended in DMEM containing 10% FCS and 10% dimethylsulfoxide (DMSO) and kept frozen in liquid nitrogen vapor according to conventional protocol (Gordon S L et al, Cryobiology. 2001 September; 43(2):182-7). After reaching 90% confluence, cells that had been plated directly onto tissue culture plates are trypsinized and subcultured in new 6-well tissue culture plates at a density of 5×104 cells/well. Cells on tissue culture plates are maintained until they reach passage 10. Cells plated onto soft polyacrylamide gels are re-fed with fresh DMEM supplemented with 10% FCS twice per 7 days. When hMSC maintained in tissue culture plates reach passage 10, hMSC stocked in liquid nitrogen vapor are thawed to generate a cell suspension.

Results

To determine the viability of hMSC subjected to long-term preservation in a quiescent state in soft gels, hMSC are stored in soft gels until hMSC maintained on tissue culture plates reach passage 10. Viability of these cells is compared with cells stocked in liquid nitrogen vapor. Cells adhered to either soft gels or tissue culture plates are trypsinized, while cells stored in liquid nitrogen are thawed, to generate a cell suspension. Viability is determined by Trypan Blue staining of the cell suspensions. Thus, soft gel storage is an efficacious means of maintaining the viability of hMSC.

To measure the proliferation potency of hMSC stored long-term incubation on soft gels, cells that have been kept on soft gels, on tissue culture plates, or kept frozen in liquid nitrogen vapor are prepared, and a BrdU incorporation assay is conducted by re-plating cells from each source on tissue culture plates coated with type 1 collagen plus fibronectin and incubating in the presence of serum and BrdU for 12 hours. Cells are fixed and immuno-stained for BrdU by incubating cells with anti-BrdU antibodies (Invitrogen).

Example 10

Use of Soft Gels for Long-Term Preservation of hMSC without Attenuating Differentiation Materials and Experimental Methods Osteoblast Differentiation Assays Passage 10 hMSC suspensions are seeded onto collagen type 1 plus fibronectin-coated 96-well tissue culture plates at a density of $10^3$ cells/well. After incubating cells in GM for 24 hours, cells are induced to differentiate into osteoblasts by switching the medium to Osteogenic Induction Medium (OIM) (GM, 50 µM ascorbic acid-2-phosphate, 10 mM p-glycerophosphate, and 100 nM dexamethasone), changing the medium every 3 days for 3 weeks. Osteoblast differentiation is evaluated by fixing the cells with acetone/citrate and staining for alkaline phosphatase activity with Fast Blue RR/naphthol (Sigma-Aldrich, Kit#85).

Results

Next, differentiation potency of hMSC subjected to long-term preservation in a quiescent state in soft gels is measured. hMSC stored on soft gels or tissue culture plates are trypsinized to make generated suspensions; in parallel, cell suspensions are prepared by thawing hMSC kept frozen in liquid nitrogen. Adipocyte differentiation is assessed as described for Example 4.

In additional studies, adipocyte production is measured after incubating hMSC directly on the soft gel, without prior plating in tissue culture dishes and trypsinization.

In additional studies, osteoclast production is measured in cell suspensions prepared from soft gels, tissue culture plates, or frozen storage.

In additional studies, osteoclast production is measured after incubating hMSC directly on the soft gel, without prior plating in tissue culture dishes and trypsinization.

Example 11

Involvement of Rho-Family Small GTP-Binding Proteins and Actomyosin System in Regulating Stem Cell Growth by Matrix Rigidity Materials and Experimental Methods Rho Family Assays Polyacrylamide gels with G' of approximately 200 Pa (soft gels) and with G' of approximately 7500 Pa (stiff gels) are prepared on glass coverslips, and gels and coverslips are coated with a mixture of type I collagen and fibronectin. Polyacrylamide gels or glass coverslips are placed in 6-well plates covered with 1% agarose gel to avoid cell adhesion outside of polyacrylamide gels or glass coverslips. $5 \times 10^4$ hMSC are seeded onto either a polyacrylamide gel or a glass coverslip, then are incubated in the presence of serum for 24 hours. Cells are subjected to a pull-down assay to investigate GTP-loading level of Rho, Rac and Cdc42 by using their Activation Assay Kit (Upstate Biotech, Charlottesville, Va.).

Transfection of Cells with Dominant Negative or Constitutively Active Rho Forms cDNA for the candidate Rho GTPase is cloned from a rat liver cDNA library, and a mutation creating a D/N- or C/A-form of a Rho protein (Qui R G et al, Proc Natl Acad Sci USA. 1995 Dec. 5; 92(25):11781-5; Lu X et al, Curr Biol. 1996 Dec. 1; 6(12):1677-84) is introduced, and a myc tag-encoding sequence is added to each cDNA. Recombinant adenovirus expressing mutant Rho-family proteins is created and used to overexpress the mutant proteins in hMSC.

Results

To further study the role of Rho-family proteins in transmitting information about the extracellular matrix, activities of Rho-family proteins are assayed in MSC grown in soft or stiff gels. Additional Rho-family proteins involved in transmitting these signals are identified.

In additional experiments, the dominant negative (D/N) form or the constitutively active (C/A) form of a Rho-family protein of interest is overexpressed in hMSC. Recombinant adenovirus expressing LacZ is utilized as a negative control. hMSC from soft gels, stiff gels, or glass coverslips are prepared, incubated for 24 hours, then left uninfected or infected with adenovirus that expresses LacZ or mutant forms of Rho-family proteins. After 36 hours of incubation, BrdU is added to the medium, and cells are incubated for an additional 12 hours in serum-containing medium, then fixed and immunostained for both myc-tag and BrdU by using anti-myc antibodies (Cell Signaling Technology, Danvers, Mass.) and anti-BrdU antibodies (Invitrogen, Carlsbad, Calif.). Comparison of the number of cells positive for BrdU staining between cells uninfected and cells infected with LacZ adenovirus is used to confirm that adenovirus infection itself has no effect on the growth of hMSC. The number of cells positive for BrdU incorporation is compared to the number positive for myc-tag staining. Down-modulation of soft matrix-induced growth arrest or rigid matrix-induced growth promotion by C/A- and D/N-forms of Rho-family proteins, respectively, indicates involvement of the overexpressed Rho-family protein in growth regulation of hMSC by matrix rigidity.

Example 12

Determining the Role of Actomyosin in Regulating Stem Cell Growth by Matrix Rigidity To study the role of actomyosin in regulating hMSC growth on soft gels before commitment to specific cell lineages, hMSC are seeded on glass coverslips coated with a mixture of collagen type 1 and fibronectin for 24 hours, then are incubated with BrdU in the presence or absence of 20 mM 2,3-butanedione monoxime (BDM), 100 µM blebbistatin or 0.25 µM/ml cytochalasin D (CD) for an additional 12 hours. Throughout the experiment, cells are incubated in the presence of serum. After the incubation, cells are fixed and immuno-stained for BrdU. The effect on hMSC growth of inhibiting myosin II by BDM or bebbistatin, or disrupting actin filaments by CD, is evaluated.

Example 13

Growth and Differentiation of hMSC in Soft 3-Dimensional Fibrin Gels

Materials and Experimental Methods

Preparation and Seeding of Fibrin Gels

Salmon fibrinogen (Searun Holdings, Freeport, Me.) is re-hydrated in $H_2O$ and diluted to 3 (for soft gel) or 18 mg/mL (for stiff gel) in 50 mM Tris, 150 mM NaCl, pH 7.4, and 400 microliter (µl) aliquots are polymerized with 2 units/mL of fish thrombin (Searun Holdings) in tissue culture wells. The rigidity of salmon fibrin gels prepared from 3 and 18 mg/mL fibrinogen are 250 Pa and 2150 Pa, respectively. $10^4$ hMSC are mixed with fibrinogen solution in DMEM containing 10% FCS before polymerization, wherein cells are incubated for 24 hours.

Results

Analysis of proliferation of MSC in soft and stiff fibrin gels is evaluated by incubating cells for an additional 12 hours in the presence of serum and BrdU, followed by fixing and immuno-staining for BrdU incorporation.

Differentiation potency of hMSC in fibrin gels is evaluated by efficiency of adipocyte differentiation. MSC in fibrin gels are induced to differentiate into adipocytes by switching the medium to Adipogenic Induction Medium ("AIM" DMEM+10% FBS, 1 micromolar (mcM) dexamethasone, 200 mcM indomethacin, 10 microgram (mcg)/ml insulin, and 0.5 mM methylisobutylxanthine) for 3 days, then maintaining cells in Adipogenic Maintenance Medium (GM, 10 mcg/ml insulin). 8 days after switching to Adipogenic Induction Medium, adipocyte differentiation is evaluated either by Oil Red 0 staining or by anti-PPARγ2 immunostaining. Percentages of cells positive for Oil Red 0 staining or PPAR72 staining are compared between soft and stiff fibrin gels.

In other experiments, protease inhibitors are added to the matrix to prevent or inhibit proteolytic degradation or other active remodeling by the cells.

Example 14

Use of hMSC of the Present Invention to Maintain Viability of Hematopoietic Stem Cells Passage 10 MSC suspensions are seeded onto collagen type 1 plus fibronectin-coated 96-well tissue culture plates at a density of $10^3$ cells/well. After incubating cells in GM for 24 hours, cells are cultured in the presence of a soft gel or matrix, as described in the above Examples. The resulting mesenchymal stem cell cultures are then added to hematopoietic stem cell cultures to maintain viability of the latter cells.

In additional studies, hMSC are incubated directly on the soft gel, without prior plating in tissue culture dishes and trypsinization.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of inducing differentiation of a mesenchymal stem cell into a cell type of interest, said method comprising the steps of:
    (a) maintaining said mesenchymal stem cell adhered onto the surface of a gel or a gel matrix and in the presence of nutrient material, wherein the surface of said gel or said gel matrix has a uniform rigidity in a range of 150-750 Pa in the microenvironment of the cell and comprises adhesion molecules, such that the cell is maintained in a quiescent state and is arrested in the cell cycle,
    wherein said quiescent state is characterized by (i) a lack of proliferation, (ii) a lack of differentiation, (iii) the ability of the cell to express proteins, and (iv) the ability of the cell to resume proliferation and differentiation upon exposure to a chemical stimulus, a mechanical stimulus, a physical factor or a combination thereof, and
    wherein the cell lacks stress fibers, and then
    (b) inducing differentiation of said mesenchymal stem cell in the quiescent state into said cell type of interest by exposing said mesenchymal stem cell to the chemical stimulus, the mechanical stimulus, the physical factor or the combination thereof.

2. The method of claim 1, wherein the chemical stimulus is an induction medium.

3. The method of claim 1, wherein the chemical stimulus is an adipogenic induction medium or an osteogenic induction medium.

4. The method of claim 1, wherein the mechanical stimulus is an increase in gel rigidity.

5. The method of claim 1, wherein the physical factor is pressure, temperature or a combination of both pressure or temperature.

6. The method of claim 1, wherein said mesenchymal stem cell is arrested in the G1 phase or the G2 phase.

7. The method of claim 1, wherein said cell type of interest is an adipocyte or an osteoblast.

8. The method of claim 1, wherein said gel or gel matrix comprises acrylamide and bisacrylamide.

9. The method of claim 1, wherein said gel or gel matrix is 2-dimensional or 3-dimensional.

10. The method of claim 1, wherein said adhesion molecules are cross-linked with said gel or gel matrix.

11. The method of claim 1, wherein said mesenchymal stem cell is a human mesenchymal stem cell.

12. The method of claim 1, wherein said gel or the gel in said gel matrix has an acrylamide:bisacrylamide mixture ratio of between about 750:1 and 6:1.

13. The method of claim 1, wherein said gel or the gel in said gel matrix has an acrylamide:bisacrylamide mixture ratio of between about 100:1 and 30:1.

14. The method of claim 1, wherein said gel or the gel in said gel matrix has a total acrylamide concentration of 3-7.5%.

15. The method of claim 10, wherein said adhesion molecules comprise collagen and fibronectin.

16. A method of inducing differentiation of a mesenchymal stem cell into a cell type of interest, said method comprising the steps of:
   (a) maintaining said mesenchymal stem cell adhered onto the surface of a gel or a gel matrix and in the presence of nutrient material, wherein the surface of said gel or said gel matrix has a uniform rigidity in a range of 150-750 Pa in the microenvironment of the cell and comprise adhesion molecules, such that the cell is artificially induced into a quiescent state and is arrested in the cell cycle,
   wherein said quiescent state is characterized by (i) a lack of proliferation, (ii) a lack of differentiation, (iii) the ability of the cell to express proteins, and (iv) the ability of the population to resume proliferation and differentiation upon exposure to a chemical stimulus, a mechanical stimulus, a physical factor or a combination thereof, and
   wherein the cell lacks stress fibers, and then
   (b) inducing differentiation of said mesenchymal stem cell in the quiescent state into said cell type of interest by exposing said mesenchymal stem cell to the chemical stimulus, the mechanical stimulus, the physical factor or the combination thereof.

17. The method of claim 16, wherein the chemical stimulus is an induction medium.

18. The method of claim 16, wherein the chemical stimulus is an adipogenic induction medium or an osteogenic induction medium.

19. The method of claim 16, wherein the mechanical stimulus is an increase in gel rigidity.

20. The method of claim 16, wherein the physical factor is pressure, temperature or a combination of both pressure or temperature.

21. The method of claim 16, wherein said mesenchymal stem cell is arrested in the G1 phase or the G2 phase.

22. The method of claim 16, wherein said cell type of interest is an adipocyte or an osteoblast.

23. The method of claim 16, wherein said gel or gel matrix comprises acrylamide and bisacrylamide.

24. The method of claim 16, wherein said gel or gel matrix is 2-dimensional or 3-dimensional.

25. The method of claim 16, wherein said adhesion molecules are cross-linked with said gel or gel matrix.

26. The method of claim 16, wherein said mesenchymal stem cell is a human mesenchymal stem cell.

27. The method of claim 16, wherein said gel or the gel in said gel matrix has an acrylamide:bisacrylamide mixture ratio of between about 750:1 and 6:1.

28. The method of claim 16, wherein said gel or the gel in said gel matrix has an acrylamide:bisacrylamide mixture ratio of between about 100:1 and 30:1.

29. The method of claim 16, wherein said gel or the gel in said gel matrix has a total acrylamide concentration of 3-7.5%.

30. The method of claim 25, wherein said adhesion molecules comprise collagen and fibronectin.

31. The method of claim 1, wherein the cell exhibits a rounded morphology.

32. The method of claim 16, wherein the cell exhibits a rounded morphology.

33. A method of inducing differentiation of a mesenchymal stem cell into a cell type of interest, said method comprising the steps of:
   (a) maintaining said mesenchymal stem cell adhered onto the surface of a gel or a gel matrix and in the presence of nutrient material, wherein the surface of said gel or said gel matrix has a uniform rigidity in a range of 150-750 Pa in the microenvironment of the cell and comprises adhesion molecules, such that the cell is maintained in a quiescent state and is arrested in the cell cycle,
   wherein said quiescent state is characterized by (i) a lack of proliferation, (ii) a lack of differentiation, (iii) the ability of the cell to express proteins, and (iv) the ability of the cell to resume proliferation and differentiation upon exposure to a chemical stimulus, a mechanical stimulus, a physical factor or a combination thereof, and
   wherein the cell is not spread, and then
   (b) inducing differentiation of said mesenchymal stem cell in the quiescent state into said cell type of interest by exposing said mesenchymal stem cell to the chemical stimulus, the mechanical stimulus, the physical factor or the combination thereof.

34. A method of inducing differentiation of a mesenchymal stem cell into a cell type of interest, said method comprising the steps of:
   (a) maintaining said mesenchymal stem cell adhered onto the surface of a gel or a gel matrix and in the presence of nutrient material, wherein the surface of said gel or said gel matrix has a uniform rigidity in a range of 150-750 Pa in the microenvironment of the cell and comprises adhesion molecules, such that the cell is maintained in a quiescent state and is arrested in the cell cycle,
   wherein said quiescent state is characterized by (i) a lack of proliferation, (ii) a lack of differentiation, (iii) the ability of the cell to express proteins, and (iv) the ability of the cell to resume proliferation and differentiation upon exposure to a chemical stimulus, a mechanical stimulus, a physical factor or a combination thereof, and
   wherein the cell has round morphology, and then
   (b) inducing differentiation of said mesenchymal stem cell in the quiescent state into said cell type of interest by exposing said mesenchymal stem cell to the chemical stimulus, the mechanical stimulus, the physical factor or the combination thereof.

35. The method of claim 1, wherein the surface of said gel or said gel matrix has a uniform rigidity in a range of 150-200 Pa.

36. The method of claim 1, wherein the surface of said gel or said gel matrix has a uniform rigidity of 200 Pa.

37. The method of claim 16, wherein the surface of said gel or said gel matrix has a uniform rigidity in a range of 150-200 Pa.

38. The method of claim 16, wherein the surface of said gel or said gel matrix has a uniform rigidity of 200 Pa.

* * * * *